US009789241B2

(12) United States Patent
Fierens et al.

(10) Patent No.: US 9,789,241 B2
(45) Date of Patent: Oct. 17, 2017

(54) SYSTEM FOR MONITORING AND CONTROLLING ORGAN BLOOD PERFUSION

(71) Applicant: MEDICAL DEVICE WORKS NV, Brussels (BE)

(72) Inventors: Joop Fierens, Dworp (BE); Kevin Jason Nackard, Flagstaff, AZ (US); Eric Thierry Jean Marcoux, Wemmel (BE); Emmanuel J. Bartholome, Uccle (BE)

(73) Assignee: MEDICAL DEVICE WORKS NV, Brussels (BE)

( * ) Notice: Subject to any disclaimer, the term of this patent is extended or adjusted under 35 U.S.C. 154(b) by 282 days.

(21) Appl. No.: 14/381,809

(22) PCT Filed: Mar. 1, 2013

(86) PCT No.: PCT/EP2013/054200
§ 371 (c)(1),
(2) Date: Aug. 28, 2014

(87) PCT Pub. No.: WO2013/128012
PCT Pub. Date: Sep. 6, 2013

(65) Prior Publication Data
US 2015/0080635 A1 Mar. 19, 2015

(30) Foreign Application Priority Data
Mar. 1, 2012 (EP) .................................... 12157765

(51) Int. Cl.
*A61M 1/34* (2006.01)
*A61M 1/36* (2006.01)
(Continued)

(52) U.S. Cl.
CPC ........... *A61M 1/34* (2013.01); *A61B 17/1204* (2013.01); *A61B 17/12036* (2013.01);
(Continued)

(58) Field of Classification Search
CPC ........ A61M 1/32; A61M 1/34; A61M 1/3455; A61M 1/3615; A61M 1/3621;
(Continued)

(56) References Cited

U.S. PATENT DOCUMENTS 6,287,273 B1 * 9/2001 Allers ................. A61M 1/3621
604/27
8,133,194 B2 * 3/2012 Szamosfalvi ....... A61M 1/3672
210/645
(Continued)

FOREIGN PATENT DOCUMENTS

WO WO 2011/097295 A1 8/2011

*Primary Examiner* — Quynh-Nhu H Vu
(74) *Attorney, Agent, or Firm* — Knobbe, Martens, Olson & Bear LLP

(57) ABSTRACT

The present invention provides a system, a method, devices and a computer implemented with a method for the monitoring and the control of a subject's organ perfusion. The present invention further provides for the use of a system, a method, devices and a computer implemented with a method for the monitoring and the control of a subject's organ perfusion.

17 Claims, 20 Drawing Sheets

(51) Int. Cl.
    *A61M 1/32*      (2006.01)
    *A61N 5/10*      (2006.01)
    *A61B 17/12*     (2006.01)
    *A61M 5/142*     (2006.01)
    *A61M 25/10*     (2013.01)
    *A61M 25/00*     (2006.01)
    *A61B 17/00*     (2006.01)

(52) U.S. Cl.
    CPC .. *A61B 17/12109* (2013.01); *A61B 17/12136* (2013.01); *A61B 17/12172* (2013.01); *A61M 1/32* (2013.01); *A61M 1/3455* (2013.01); *A61M 1/367* (2013.01); *A61M 1/3615* (2014.02); *A61M 1/3621* (2013.01); *A61M 5/142* (2013.01); *A61M 25/0074* (2013.01); *A61M 25/10* (2013.01); *A61M 25/1018* (2013.01); *A61N 5/1002* (2013.01); *A61B 2017/00893* (2013.01); *A61B 2017/1205* (2013.01); *A61B 2017/12054* (2013.01); *A61M 25/007* (2013.01); *A61M 25/0075* (2013.01); *A61M 2025/105* (2013.01); *A61M 2025/1052* (2013.01); *A61M 2205/3303* (2013.01); *A61M 2205/3344* (2013.01)

(58) Field of Classification Search
    CPC ............ A61M 1/367; A61M 2025/105; A61M 2025/1052; A61M 2205/3303; A61M 2205/3344; A61M 25/007; A61M 25/0074; A61M 25/0075; A61M 25/10; A61B 17/12036; A61B 17/1204; A61B 17/12109; A61B 17/12136; A61B 17/12172; A61B 2017/00893; A61B 2017/1205; A61B 2017/12054
    See application file for complete search history.

(56) References Cited

U.S. PATENT DOCUMENTS

| | | |
|---|---|---|
| 2005/0101934 A1 | 5/2005 | Meiser et al. |
| 2009/0112184 A1 | 4/2009 | Fierens et al. |
| 2009/0157058 A1* | 6/2009 | Ferren ................. A61B 5/0031 604/891.1 |
| 2011/0282274 A1 | 11/2011 | Fulton, III |
| 2012/0150090 A1* | 6/2012 | Szamosfalvi ....... A61M 1/3672 604/6.07 |

* cited by examiner

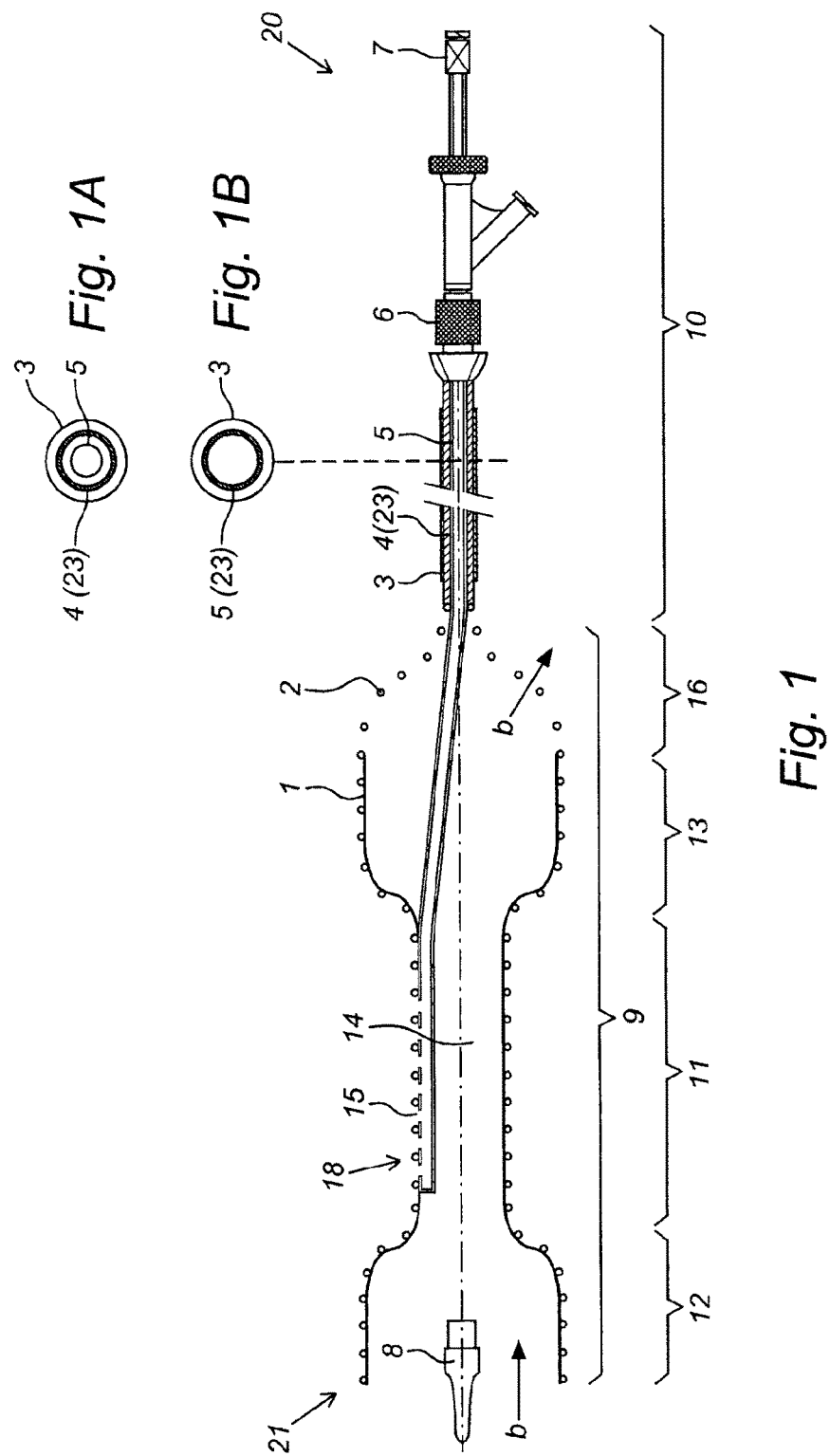

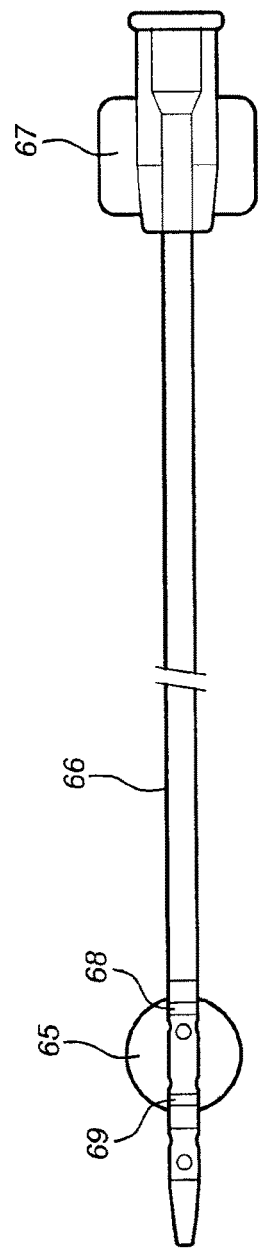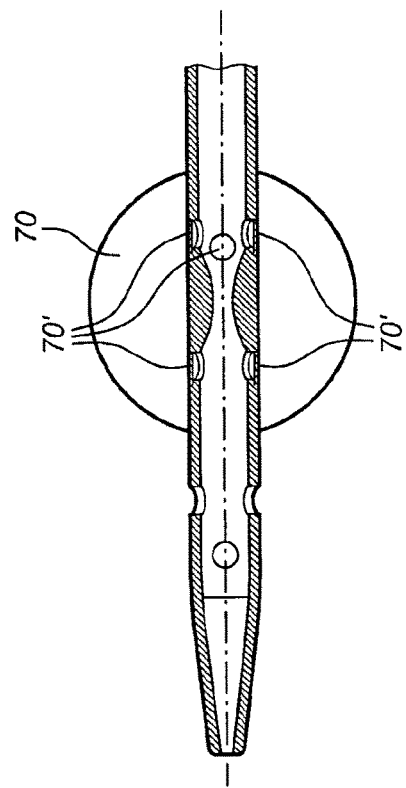
Fig. 11A
Fig. 11B

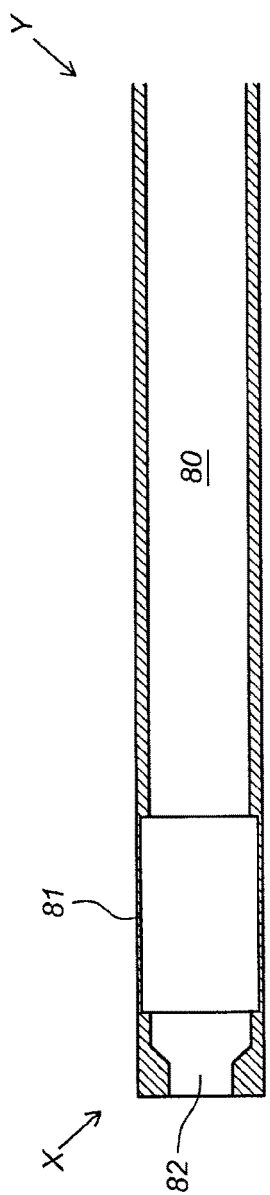
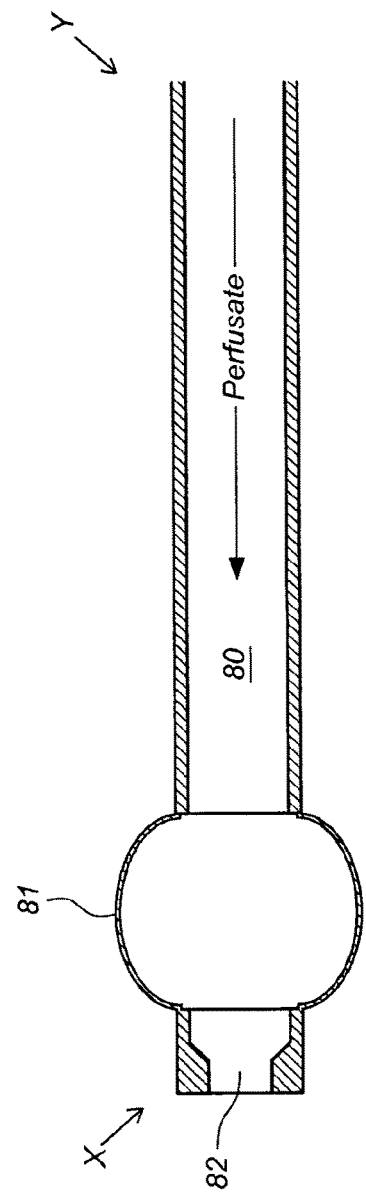

SYSTEM FOR MONITORING AND CONTROLLING ORGAN BLOOD PERFUSION

CROSS-REFERENCE TO RELATED APPLICATIONS

This application is the U.S. National Phase under 35 U.S.C. §371 of International Application PCT/EP2013/054200, filed Mar. 1, 2013, which claims priority to EP 12157765.4, filed Mar. 1, 2012.

FIELD OF THE INVENTION

The present invention generally relates to the field of medical treatment systems. More particularly, the present invention relates to a system, devices and methods for monitoring and controlling the perfusion of an organ of a subject.

BACKGROUND

Currently, the most common modes of treatment of primary and secondary cancer of organs consist of surgical resection, radiotherapy and/or systemic chemotherapy. The side effects of cytotoxic agents associated with systemic chemotherapy are well known. Some common toxicities are bone marrow suppression leading to neutropenia, anaemia and thrombocytopenia; hair follicle cell damage leading to alopecia; induction of apoptosis of gastrointestinal crypt cells leading to diarrhea and oral ulceration. Additionally, different drug classes can cause other toxicities including heart damage, peripheral nerve damage leading to sensory-motor neuropathy, renal damage, and pulmonary fibrosis.

For many organ cancers, the only curative treatment option is surgical resection. However, surgical resection is not always an option. Often the cancer is not detected until it is in an advanced state and has metastasized throughout the organ making it unresectable. Systemic chemotherapy in these cases has disappointing response rates with moderate increase in patient survival. Chemotherapy doses are often limited by their toxic side effects on other organs. Therefore, it is desirable to apply the chemotherapy only to the organ being treated. Treating an isolated organ can potentially enable higher doses as the drug will be concentrated in the target organ and significantly reduces or eliminates systemic toxicity. Additionally, isolated organ perfusion allows for multiple treatments in a relatively short time period as the body does not need to recover from the lasting effects of systemic toxicity.

Isolated organ perfusion has been performed using typical surgical and interventional techniques. Isolated surgical organ perfusion has been performed on the liver with encouraging results. However the trauma of surgery performed to isolate the organ prevents multiple applications of chemotherapy. Moreover, an organ cannot be completely isolated from the systemic blood flow as, even by stopping the main blood inflow and outflow; the organ will communicate with the systemic circulation via collateral connections or vessels. This is for instance the case for the liver, which besides the main vessels being the hepatic artery, the portal vein and the vena cava, is provided with collateral vessels which communicate with the systemic blood circulation. The perfused therapeutic agent will be at least partially conveyed to the patient's non-targeted organs through the systemic blood flow. This is disadvantageous for the patient as (i) it leads to a dilution of the perfused therapeutic agent dose which inhibits the effect on the targeted organ (ii) it limits the maximum dose that can be perfused to a targeted organ to the maximum dose leaked out of said organ which can be accepted by other non-targeted organs of the patient's body.

In addition, in reaction to some diseases such tumors which make organ blood flow difficult, the blood will find a way to circumvent the tumor by creating and/or connecting to other tissues and/or organs. In this case the practitioner is not aware of the newly developed connections. Said connections increase the leakage rate of the therapeutic agent or the chemotherapy drug from the perfused organ to the systemic blood flow. This result in systemic toxicity or higher blood loss during the intervention which might, in some cases, be dangerous for the treated subject and the functioning of the whole subject's body.

Up to date, the local perfusions need a large group of clinical specialist to execute a full procedure: interventional radiologist, anesthesiologist, nuclear specialist, perfusionist, oncologist, nurses. Moreover, due to the full manual control, the procedure could take more than four hours to be completed. The local perfusions have to be performed 2 to 5 times per patient. All these factors result in a treatment which is expensive. Therefore, the treatment cannot be made available due to all patients for economic reasons.

The aim of the present invention is to provide a solution to at least part of the above mentioned problems. The present invention provides a system, devices and a method for monitoring and controlling a subject's organ perfusion. The method of the invention overcomes the described problem as it provides a more patient safe and cheaper treatment.

SUMMARY OF THE INVENTION

In a first aspect, the present invention provides a system for the monitoring and the control of a subject's organ perfusion. The system comprises:
  optionally at least one therapeutic agent,
  at least one first retrievable medical device, for the simultaneous or the separate perfusion and occlusion of the vessel of the organ inflow, comprising a body having a distal end, a proximal end, at least one lumen extending between the proximal end and the distal end, at least one opening which is in fluid communication with the lumen for delivering a fluid to said vessel and at least one expandable balloon coupled with the body of the device,
  at least one second retrievable medical device for isolating and collecting the organ outflow, said device is provided with a distal end and a proximal end; said second medical device comprises a catheter suitable for deploying an expanding member; the proximal end of the expanding member is attached to the distal end of the catheter,
  a fluid storage reservoir having at least one inlet and at least one outlet, said inlet is suitable to be connected to the proximal end of the second retrievable medical device and said outlet is suitable to be connected to the proximal end of the first retrievable medical device medical,
  at least one pump for withdrawing fluid from the organ and directing said fluid to the fluid storage reservoir through the inlet of said fluid storage reservoir,
  at least one pump for withdrawing fluid from the fluid storage reservoir at a determined flow rate and directing said fluid to the organ inflow, optionally, at least one marker for real time monitoring of the leak rate from the organ to the systemic blood circulation, at least one marker detector positioned upstream of the inlet of the fluid storage reservoir, at least one marker detector positioned in at least one vessel of the systemic blood circulation, at least one volume sensor positioned in the fluid storage reservoir, at least one pressure detector for measuring the fluid pressure inside the organ to be perfused, and at least one interface for receiving and presenting output system data and for controlling and/or adjusting input system data, wherein the output system data comprises the data collected by the pressure detector and the marker detectors; and the input system data comprises the fluid flow rate to be withdrawn from the fluid storage reservoir which is directed to the organ inflow. The output system data further comprises the volume of fluid present in the fluid storage container.

In a second aspect, the present invention provides a method for the monitoring and the control of a subject's organ perfusion comprising the steps of:

(a) introducing a first retrievable medical device in the organ inflow vessel for the simultaneous or the separate perfusion and occlusion of said inflow vessel, said first medical device comprises a body having a distal end, a proximal end, at least one lumen extending between the proximal end and the distal end, at least one opening which is in fluid communication with the lumen for delivering a fluid said vessel; and at least one expandable balloon coupled with the body of the device, (b) introducing a second retrievable medical device for isolating and collecting the organ outflow, said second medical device is provided with a distal end and a proximal end and comprises a catheter suitable for deploying an expanding member; the proximal end of the expanding member is attached to the distal end of the catheter; said expanding member comprises a carrier and a liquid-impermeable liner, said liner is bonded to the carrier over at least a part of the length of said carrier, (c) connecting the first and the second retrievable medical devices to a fluid storage reservoir having an inlet and an outlet, wherein the proximal end of the second retrievable medical device is connected to the inlet of the fluid storage reservoir and the proximal end of the first retrievable medical device is connected to the outlet of said fluid storage reservoir, (d) measuring fluid pressure inside the organ using at least one pressure detector, (e) withdrawing fluid from the organ and directing said fluid to the fluid storage reservoir through the inlet of said fluid storage reservoir, (f) withdrawing fluid from the fluid storage reservoir and directing said fluid to the organ inflow, (g) adjusting the fluid withdrawal rates of steps (d) and (e) such as the fluid pressure inside the organ is lower than the systemic blood pressure, (h) adding at least one marker and/or at least one therapeutic agent to the fluid withdrawn from the fluid storage reservoir and directed to the organ inflow, (i) monitoring the leakage rate, from the organ to the systemic blood flow, using marker detectors, whereby at least one marker detector is positioned upstream of the inlet of the fluid storage reservoir and at least one marker detector is positioned in at least one vessel of the systemic blood circulation, and (j) retrieving the medical devices of step (a) and step (b) respectively from the organ inflow vessel and the organ outflow vessel.

In third aspect, the present invention provides a computer implemented with a method for the monitoring and the control of a subject's organ perfusion system, said system comprises at least one pressure detector for measuring fluid pressure inside the organ, outflow tubings for withdrawing fluid from said organ and inflow tubings for delivering fluid to the organ, wherein the method comprises the steps of:

receiving output system data from the system whereby the output system data comprises the fluid pressure inside the organ, a fluid flow rate at which fluid is withdrawn from the organ, an amount of a marker present in the fluid flowing in the outflow tubings, the amount of marker present in the systemic blood flow of the subject, processing the received output system data, and sending input system data whereby said data comprises a determined fluid flow rate at which fluid is delivered to the organ through the inflow tubings of the system.

In a fourth aspect, the present invention provides for the use of a system as described above, for the monitoring and the control of a subject's organ perfusion.

In a fifth aspect, the present invention provides for the use of a method as described above, for the monitoring and the control of a subject's organ perfusion.

In a sixth aspect, the present invention provides for the use of a computer implemented with a method as described above, for the monitoring and the control of a subject's organ perfusion.

The present invention presents several advantages as it allows to monitor and to control the perfusion of an organ of a subject and provides a tool for the real time evaluation, measurement, control and monitoring of the leakage rate of the therapeutic agent from the perfused organ to the systemic blood flow and the other organs of the subject's body. The invention allows identification of collateral flow and in which direction said flow is running; thereby knowing in real time if there is communication from the perfused organ to the systemic blood and vice versa. The invention also allows the practitioner to react immediately in case of a high dilution of the therapeutic agent or when approaching reaching toxic systemic levels of said therapeutic agent. The real time measurement results of the leakage rate will drive the perfusion parameters to minimize the collateral flows, and should assure that adequate action is taken in case certain limits are exceeded. Said limit is for example the amount or the concentration of the therapeutic agent that can be present in the systemic blood flow. Hence, the present invention provides improved effectiveness of organ perfusion and assures patient safety when an organ is locally treated with high dose of therapeutic agents. The delivery of said high dose is also made possible by the use of the present invention which is not offered by other systems and/or methods of the prior art.

In addition, the present invention provides a non-invasive method for organ perfusion which allows repetitive treatment of the organ. Moreover, using the present invention, a small number of practitioners is required for carrying out the perfusion of the organ. The perfusion is hence less expensive for the subjects.

DESCRIPTION OF THE FIGURES

Further features, advantages and objects of the present invention will become apparent for the skilled person when reading the following detailed description of embodiments of the present invention, when taken in conjunction with the figures of the enclosed drawings.

FIG. 1 illustrates an embodiment of the second medical device of the present invention in the expanded state comprising a tubular member (dumb-bell shaped) attached to a catheter. FIG. 1A shows a transverse cross-section across the catheter where the pusher means is a pusher rod. FIG. 1B shows a transverse cross-section across the catheter where the pusher means is formed from the wall of the inner tube.

FIGS. 3 C and D illustrate the use of the second medical device for the delivery of a therapeutic agent to the right and left lung respectively. FIGS. 3 E and F illustrate the use of the second medical device having a bell shape for the delivery of a therapeutic agent to the right and left lung respectively.

FIG. 11A and FIG. 11B illustrates an embodiment of the first medical device.

FIG. 12A and FIG. 12B longitudinal cross-section view of the first medical device

DETAILED DESCRIPTION OF THE INVENTION

Figure 1C:
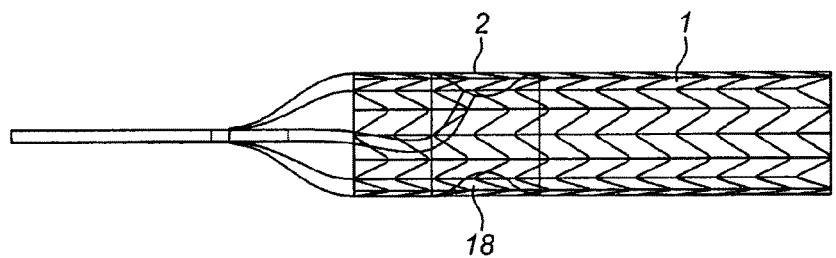
FIG. 1C illustrates another embodiment of the second medical device of the present invention in the expanded state comprising a tubular member (dumb-bell shaped) attached to a catheter. The liner is attached to the inner wall of the tubular member.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings: "A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The term "therapeutic agent" is used herein to refer to a treatment fluid or particles delivered to a patient's organ.

The terms "particles", "microspheres" and "beads" are used herein as synonyms and refer to an object that is substantially spherical in shape and has a diameter less than 1 millimeter.

The terms "lateral" and "collateral" are used herein as synonyms. The terms "control unit" and "processing unit" are used herein as synonyms.

The term "glass" refers to a hard, brittle, non-crystalline, inorganic substance, which is usually transparent; glasses are often made by fusing silicates with soda, as described by Webster's New World Dictionary. Ed. Guralnik, D B 1984.

The terms "inflow" and "outflow" herein refer respectively to the blood flowing inside an organ and the blood flowing outside an organ.

The system, devices and method of the present invention will be further detailed for a treatment of the liver and/or the lungs. However, any other organ can be treated using said system, devices and method of the present invention.

In a first aspect, the present invention provides a system for the monitoring and the control of a subject's organ perfusion. A preferred embodiment of the system is presented in FIG. 14. Said system comprises optionally at least one therapeutic agent.

The system further comprises at least one first retrievable medical device, for the simultaneous or the separate perfusion and occlusion of the vessel of the organ inflow, comprising a body having a distal end, a proximal end, at least one lumen extending between the proximal end and the distal end, at least one opening which is in fluid communication with the lumen for delivering a fluid to said vessel and at least one expandable balloon coupled with the body of the device.

The system further comprises at least one second retrievable medical device for isolating and collecting the organ outflow, said device is provided with a distal end and a proximal end; said second medical device comprises a catheter suitable for deploying an expanding member; the proximal end of the expanding member is attached to the distal end of the catheter.

The system further comprises a fluid storage reservoir 107 having at least one inlet and at least one outlet, said inlet is suitable to be connected to the proximal end of the second retrievable medical device and said outlet is suitable to be connected to the proximal end of the first retrievable medical device medical. The fluid storage reservoir is used for the storage of the fluid which is withdrawn from the perfused organ via the organ outflow or the organ outflow vessel and which will be delivered to the organ via the organ inflow or the organ inflow vessel. Said fluid can be blood, blood supplemented with a marker, blood supplemented with a therapeutic agent, blood supplemented with a marker and with a therapeutic agent, a physiologic solution or any combination thereof. In a preferred embodiment, from 0 to 5 liters, preferably from 0.5 to 4 liters, more preferably from 0.5 to 3 liters of fluid can be stored in the fluid storage reservoir. In a preferred embodiment, the total fluid volume flowing through the system is at least 10 cc, preferably at least 20 cc, more preferably at least 40 cc, most preferably at least 50 cc. The maximum volume flowing through said system is at most 1000 cc, preferably at most 800 cc, more preferably at most 600 cc, even more preferably at most 500 cc, most preferably at most 300 cc.

In a preferred embodiment, the inlet of the fluid storage reservoir is suitable to be connected to the proximal end of the second retrievable medical device using outflow tubings 102 and the outlet of the fluid storage reservoir 107 is suitable to be connected to the proximal end of the first retrievable medical device medical using inflow tubings 103. In a preferred embodiment, said tubings are preferably made from silicon or any silicon like material known to the person skilled in the art.

The system further comprises at least one pump 104,105 for withdrawing fluid from the organ 101 at a determined flow rate and directing said fluid to the fluid storage reservoir 107 through the inlet of said fluid storage reservoir 107. At least one pump 108 for withdrawing fluid from the fluid storage reservoir 107 at a determined flow rate and directing said fluid to the organ 101 inflow. Said pumps can be of similar type or of different type. The number and type of pumps required is dependent upon the organ being treated.

It is possible for a single pump to pull blood from several different vessels, as desired by the practitioner.

The pumps can be of any type and are selected from the group comprising roller pumps, centrifugal pumps, syringe pumps, metering pumps or any other pumps known to the person skilled in the art. Preferably said pumps are of the same type. More preferred said pumps are centrifugal pumps. The person skilled in the art will appreciate that the withdrawal fluid rate flow from the organ and the withdrawal fluid flow rate from the fluid storage reservoir 107 are adapted according to the type of the used pump. If a roller pump issued, it is preferable to reduce the flow rate by using a damping system for instance.

The system optionally comprises, at least one marker for real time monitoring of the leak rate from the organ 101 to the systemic blood circulation.

The system further comprises at least one marker detector 119 positioned upstream of the inlet of the fluid storage reservoir 107. At least one marker detector 120 positioned in and/or near at least one vessel of the systemic blood circulation and/or over an area of the subject's body with high blood flow that is sufficiently far away from the organ being treated.

The system further comprises at least one pressure detector 123 for measuring the fluid pressure inside the organ 101 to be perfused. Said pressure detector is positioned inside the organ to be perfused or is connected to the organ to be perfused. The detector can be of any type known to the person skilled in the art.

The system further comprises at least one volume sensor positioned in the fluid storage reservoir 107. Said sensor is used to provide the practitioner with a continuous monitoring of the fluid volume inside the fluid reservoir storage. By monitoring said volume, the practitioner can react in the event fluid volume inside said reservoir has to be adjusted to reach a predetermined upper and/or lower limit.

Said system might also comprise at least one flow meter. A flow meter 115,116 might be used for determining the flow rate at which fluid is withdrawn from the organ. Another flow meter 113,114 might be used to determine the flow rate at which the fluid withdrawn from the organ is entering the fluid storage reservoir. Another flow meter might be used for determining the flow rate at which fluid is withdrawn from the fluid storage reservoir. An extra flow meter might be used for determining the flow rate at which fluid is entering the organ. Sensors might also be used for measuring the temperature of the fluids entering and/or exiting the organ and/or the fluid storage reservoir. Other sensors might be used for determining the oxygen level of the fluids entering and/or exiting the organ and/or the fluid storage reservoir.

The system further comprises at least one interface for receiving and presenting output system data and for controlling and/or adjusting input system data.

The output system data comprises the data collected by the pressure detector 123 which comprises the fluid flow pressure inside the organ; data collected by the different flow meters which comprises the flow rates of the fluid exiting the organ and/or exiting the fluid storage reservoir and/or the flow rates of the fluid entering the organ and/or entering the fluid storage reservoir, data collected by sensors for measuring the temperature of the fluid entering the organ and/or fluid exiting the organ and/or fluid entering the fluid storage reservoir and/or fluid exiting the fluid storage reservoir; the level of oxygen in the fluid entering the organ and/or fluid exiting the organ and/or fluid entering the fluid storage reservoir and/or fluid exiting the fluid storage reservoir and/or any other data collected by any sensors and/or detectors and/or meters used in the system of the invention. The output system data further comprises the data collected by the marker detectors 104, 105 which comprises the amount of marker present in the fluid withdrawn from the organ and the amount of marker present in the systemic blood circulation. The detected amount of marker in the systemic blood flow provides the practitioner with an evaluation of the fluid leakage rate from the organ to the systemic blood flow. It is hence possible for the practitioner to react and intervene whenever the leakage rate is esteemed to be high and/or presenting a toxic risk for the subject. The output system data further comprises the volume of fluid present in the fluid storage container.

The input system data comprises the fluid flow rate to be withdrawn from the fluid storage reservoir 107 which is directed to the organ inflow. The input system might further comprise data collected by the different flow meters which comprises the flow rates of the fluid entering the organ, data collected by sensors for measuring the temperature of the fluid entering the organ and/or fluid exiting the fluid storage reservoir and/or data collected by the sensors measuring the the fluid volume in the fluid storage reservoir 107; the level of oxygen in the fluid entering the organ and/or fluid exiting the fluid storage reservoir. In a preferred embodiment, the input system data is, at least partially, manually adjusted by the practitioner. For instance, in the event that a high leakage rate of the fluid to the systemic blood circulation is observed, the practitioner can manually decrease the flow rate at which fluid is withdrawn from the fluid storage reservoir and hence the flow rate of the fluid entering the perfused organ.

In a preferred embodiment, the system further comprises a processing unit 112 *i* for adjusting the fluid flow rate which will be withdrawn from the fluid storage reservoir and directed to the organ inflow. Said processing unit 112 *i* is implemented with a method for receiving and processing the output system data and sending a signal to the pump comprising the input system data. This allows automatisation of the perfusion, thereby considerably reducing the number of practitioners required during the perfusion. In a preferred embodiment, the method comprises an algorithm.

In a preferred embodiment, the output system data received by the processing unit 112 *i* comprises the fluid pressure inside the organ, the fluid flow rate at which fluid is withdrawn from the organ, the amount of marker measured by the detector positioned upstream of the inlet of the fluid storage reservoir and the amount of marker measured by the detector positioned in at least one vessel of the systemic blood circulation. The output system data further comprises the volume of fluid present in the fluid storage container. In addition, the output system data received by the processing unit 112 *i* might further comprise all the data described above.

In a preferred embodiment, the input system data comprises a determined fluid flow rate at which fluid is withdrawn from the fluid storage reservoir and directed to the organ inflow. In addition, the input system data received by the processing unit 112 *i* might further comprise all the data described above.

In a preferred embodiment, the determined fluid withdrawal flow rate from the fluid storage reservoir is determined such as to maintain the fluid pressure inside the organ lower than the pressure of the systemic blood flow.

In a preferred embodiment, the marker is selected from the group comprising radiomarkers, dyes such as Indocyanine Green, the therapeutic agent itself, a therapeutic agent derivative, alkaline phosphatase (ALP), 5' nucleotidase, gamma glutamyl transpeptidase (GGT), Alanine amino-transferase (ALT, also known as SGPT), Aspartate amino-transferase (AST, also known as SGOT), Prothrombin time (PT) and blood clotting tested via INR tests, albumin, bilirubin.

In a preferred embodiment, the marker detectors 119,120 allow indirect measurement of the marker amount. Said detector allows collection of a fluid sample. Said fluid sample is analyzed to determine its marker content. Preferably said sample is immediately analyzed in order to ensure a continuous evaluation and control of leakage rate of the fluid from the organ to the systemic blood circulation.

In a preferred embodiment, the marker detectors 119,120 allow direct measurement of the marker amount. Said markers are suitable to detect the amount of marker in the fluid withdrawn from the organ and in the systemic blood flow. The different markers and the corresponding suitable detector are listed in table 1. It is to be understood that the markers listed herein are suitable to be used for liver perfusion and that any other suitable marker suitable to be used for liver perfusion or any other organ and the corresponding marker detector known to the person skilled in the art can be used in the system of the present invention.

TABLE 1 markers and suitable marker detector

| Marker | Marker detection | Used method or technique |
|---|---|---|
| Radiomarkers such as $^{99m}$Tc | Direct measurement | Use of NaI crystal scintillation counter |
| dyes such as Indocyanine Green | Direct measurement | Use finger detector |
| the therapeutic agent itself | Indirect measurement | Drug dependent |
| a therapeutic agent derivative | Indirect measurement | Drug dependent |
| alkaline phosphatase | Direct measurement | Serum alkaline phosphatase level |
| gamma glutamyl transpeptidase (GGT) | Direct measurement | Clinical Biochemistry |
| ALT | Direct measurement | Clinical Biochemistry |
| AST | Direct measurement | Clinical Biochemistry |
| PT | Direct measurement | Clinical Biochemistry |
| INR | Direct measurement | Clinical Biochemistry |
| albumin | Direct measurement | Clinical Biochemistry |
| bilirubin | Direct measurement | Clinical Biochemistry |

Alanine aminotransferase (ALT, also known as SGPT). This enzyme plays a role in processing proteins. When the liver is injured or inflamed, levels of ALT in the blood usually rise.

Aspartate aminotransferase (AST, also known as SGOT). This enzyme is found in several body tissues, including the liver. Like ALT, AST also plays a role in processing proteins. If the liver is injured, the body releases AST into the bloodstream.

Alkaline phosphatase (ALP). This enzyme is found in several body tissues, including the liver. Kids and teenagers normally have higher levels of ALP than adults because of bone growth. But ALP levels higher than normal can be a sign of liver diseases or blocked bile ducts.

Total bilirubin and direct bilirubin. Bilirubin is a byproduct of the normal breakdown of red blood cells. It usually passes through the liver and is flushed from the body. But if that doesn't happen due to a liver disease, bilirubin levels in the blood can rise and the skin can take on the yellow discoloration known as jaundice. Tests for bilirubin may be total (measuring the level of all of the bilirubin in the blood) or direct (measuring only bilirubin that has been processed by the liver and attached to other chemicals).

Albumin and total protein. Liver function tests include measuring albumin (the major blood protein produced by the liver), as well as the total amount of all proteins in the blood. When there's a problem with the liver, there can be changes in the amounts of albumin and other proteins it produces.

Prothrombin time and INR. The prothrombin time (also called the "protime" or PT) and the INR are tests used to assess blood clotting. Blood clotting factors are proteins made by the liver. When the liver is significantly injured, these proteins are not produced normally. The PT and INR are also useful liver function tests since there is a good correlation between abnormalities in coagulation measured by these tests and the degree of liver dysfunction. The values for the PT are usually expressed in seconds and compared to a control patient's blood (normal +/−2 seconds of control).

Figure 14:
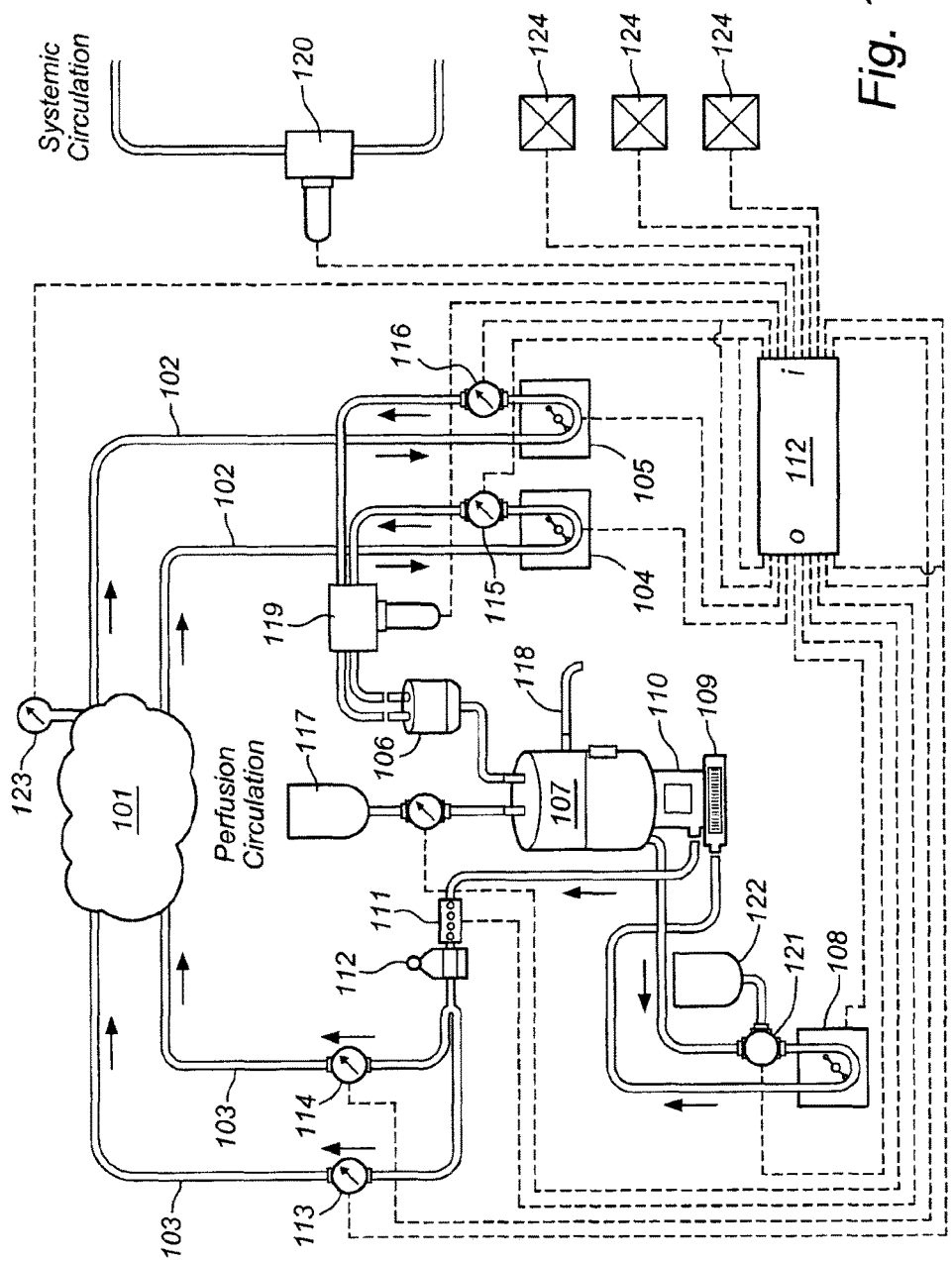
FIG. 14 is a schematic view of a system that can be used to perfuse a medical treatment through an organ. The system can be controlled by a processing unit.

In a preferred embodiment, the system further comprises at least one oxygenator 110 positioned downstream of the outlet of the fluid storage reservoir 107 (FIG. 14). In a preferred embodiment, the system further comprises at least one heat exchanger 109 positioned downstream of the outlet of the fluid storage reservoir 107. Said heat exchanger 109 might be positioned downstream said oxygenator 110 (FIG. 14).

In a preferred embodiment, the system further comprises at least one filter 106 positioned upstream of the inlet of the fluid storage reservoir 107 (FIG. 14). Said filter is used for filtering the fluid withdrawn from the organ, thereby removing any bubbles or micro emboli that may be present in said fluid. This is advantageous as it reduces the risk of having emboli in the systemic blood flow of the subject. In a preferred embodiment, the filter is provided with a reservoir which serves as a buffer for the fluid storage reservoir.

In a preferred embodiment, the system further comprises one or more third retrievable medical device for the occlusion of the organ vessels, said device having a proximal end, a distal end, a lumen extending between said proximal and said distal end, a lumen and at least one inflatable balloon for the occlusion of a vessel. The organ to be perfused might be provided with more than one main vessel; said vessels are preferably occluded for better isolation of said organ. For instance, the liver is connected to the systemic blood flow by the following vessels: the vena cava, the hepatic artery and the portal vein.

In a preferred embodiment, the first medical device and/or the second medical device and/or the third medical device are percutaneously introduced into the different organ vessels; which is a non-invasive introduction thereby permitting repetitive perfusion of the organ.

In a preferred embodiment, the system further comprises at least one container 122 containing a physiologic solution which is optionally delivered to the organ 101 for washing said organ before the start of the perfusion and/or when said perfusion is completed. Said container might be connected to a pump 108 for the withdrawal of physiologic solution at a determined flow rate. The pump is suitable to be connected to the organ inflow. The container 122 might be connected to the inflow tubings 103 and/or to the processing unit 122i which will send a signal to actuate a valve 121. Said valve 121 is positioned between the container 122 and the pump 108 and is used for allowing or preventing the withdrawal of the physiologic solution from said container 122. The valve can also be manually actuated by the practitioner.

In a preferred embodiment, the system further comprises at least one injection manifold 111 for adding a marker and/or a therapeutic agent to the fluid withdrawn from the fluid storage reservoir and directed to the organ inflow. Said marker and/or therapeutic agent might be added directly to the fluid storage reservoir. The amount and/or the concentration of said marker and/or therapeutic agent is determined by the practitioner according to different parameters, such as the organ to be perfused and the disease to be cured.

In a preferred embodiment, the system further comprises at least one bubble trap 112. The system is suitable for the connection of other sensors and/or actuators and/or pumps and/or detectors as needed and in accordance with the organ to be perfused. Said sensors and/or actuators and/or pumps and/or detectors might be used for conducting in-process assays to determine drug concentrations or for blood analysis as needed.

In a preferred embodiment, the system further comprises at least one blood source 117 connected to the fluid storage reservoir 107 for adding blood to said reservoir if needed. The person skilled in the art will appreciate that the added blood is of the same type as the subject's blood.

Figure 4:
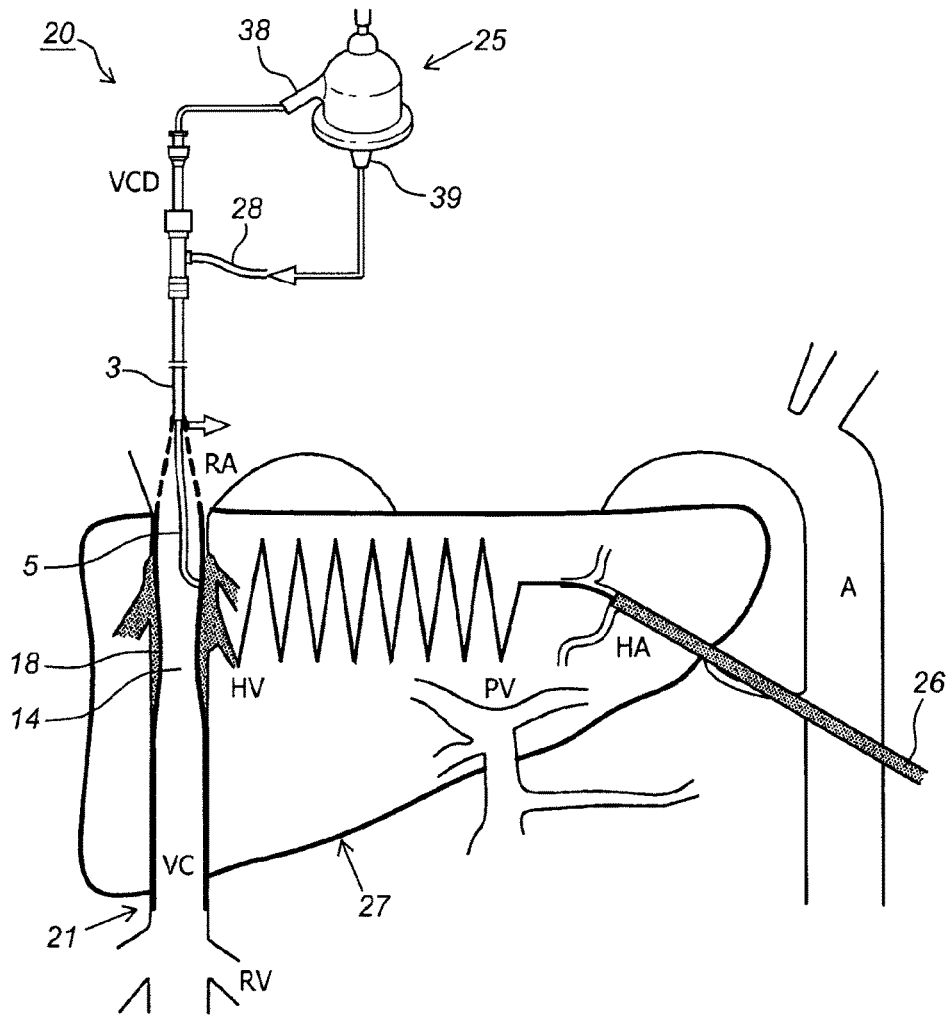
FIG. 4 illustrates an embodiment of the kit wherein the first medical device, the second medical device and the separation device are used for delivering a therapeutic agent and removing the therapeutic agent excess from the liver.

In a second aspect, the present invention provides a method for the delivery a therapeutic agent to an organ blood flow and the removal of the excess of said therapeutic agent from said organ blood flow. The method comprises the steps of (a) introducing a first medical device (26, FIG. 4) in the organ inflow vessel, (b) introducing a second medical device in the organ outflow vessel, without obstruction of the systemic blood flow, (c) controlling the infusion and/or the perfusion flow, thereby optimizing the settings for maximal local therapeutic effects, with minimal collateral damage, (d) injecting the therapeutic agent into the organ inflow using the first medical device, (e) collecting the organ blood outflow using the second medical device, (f) circulating the drug loaded perfusate, thereby optimizing the therapeutic results by adjusting the physical parameters and adding or removing therapeutic additives, and (g) separating the therapeutic agent excess from the collected organ vein using the separation device. The method further comprises the step of (h) redirecting the filtered blood into the organ blood flow if an extracorporeal blood filtration is performed.

In a preferred embodiment, once the organ has been isolated from the systemic circulation, the method uses a system where the intra-organ blood pressure and leak rate to the systemic circulation are monitored and used in a processing unit to control the perfusion dynamics of a therapeutic agent perfusion i.e. pump speed and/or pressures, flow balancing and metering and, potentially, drug administration.

In a preferred embodiment, the present invention provides a method for the monitoring and the control of a subject's organ perfusion. Said method comprises the steps of:

(a) introducing a first retrievable medical device in the organ inflow vessel for the simultaneous or the separate perfusion and occlusion of said inflow vessel, said first medical device comprises a body having a distal end, a proximal end, at least one lumen extending between the proximal end and the distal end, at least one opening which is in fluid communication with the lumen for delivering a fluid said vessel; and at least one expandable balloon coupled with the body of the device, (b) introducing a second retrievable medical device for isolating and collecting the organ outflow, said second medical device is provided with a distal end and a proximal end and comprises a catheter suitable for deploying an expanding member; the proximal end of the expanding member is attached to the distal end of the catheter; said expanding member comprises a carrier and a liquid-impermeable liner, said liner is bonded to the carrier over at least a part of the length of said carrier, (c) connecting the first and the second retrievable medical devices to a fluid storage reservoir 107 having an inlet and an outlet, wherein the proximal end of the second retrievable medical device is connected to the inlet of the fluid storage reservoir 107 and the proximal end of the first retrievable medical device is connected to the outlet of said fluid storage reservoir 107. Said fluid storage reservoir is as described above for the system of the invention. The connection of the fluid storage reservoir to the first medical device and to the second medical device is also as described above for the system of the invention.

(d) measuring fluid pressure inside the organ 101 using at least one pressure detector 123. Said pressure detector is positioned inside the organ to be perfused or is connected to the organ to be perfused. The detector can be of any type known to the person skilled in the art.

(e) withdrawing fluid from the organ 101 and directing said fluid to the fluid storage reservoir 107 through the inlet of said fluid storage reservoir 107. The flow rate at which said fluid is withdrawn from the organ and directed to the fluid storage reservoir is continuously measured by at least one flow meter 115,116.

(f) withdrawing fluid from the fluid storage reservoir 107 and directing said fluid to the organ 101 inflow. The flow rate at which said fluid is withdrawn from the fluid storage reservoir and directed to the organ is continuously measured by at least one flow meter 113,114.

(g) adjusting the fluid withdrawal rates of steps (d) and (e) such as the fluid pressure inside the organ is lower than the systemic blood pressure.

(h) adding at least one marker and/or at least one therapeutic agent to the fluid withdrawn from the fluid storage reservoir and directed to the organ inflow. Said at least one marker and/or at least one therapeutic agent might be added into the fluid storage reservoir 107.

(i) monitoring the leakage rate, from the organ 101 to the systemic blood flow, using marker detectors, whereby at least one marker detector 119 is positioned upstream the inlet of the fluid storage reservoir 107 and at least one marker detector 120 is positioned in at least one vessel of the systemic blood circulation. The marker and the marker detectors are as described above for the system of the invention.

(j) retrieving the medical devices of step (a) and step (b) respectively from the organ inflow vessel and the organ outflow vessel.

In a preferred embodiment, the practitioner is capable of controlling the perfusion method through at least one interface for receiving and presenting output system data and for controlling and/or adjusting input system data.

The output system data comprises the data collected by the pressure detector 123 which comprises the fluid flow pressure inside the organ; data collected by the different flow meters which comprises the flow rates of the fluid exiting the organ and/or exiting the fluid storage reservoir and/or the flow rates of the fluid entering the organ and/or entering the fluid storage reservoir, data collected by sensors for measuring the temperature of the fluid entering the organ and/or fluid exiting the organ and/or fluid entering the fluid storage reservoir and/or fluid exiting the fluid storage reservoir; the level of oxygen in the fluid entering the organ and/or fluid exiting the organ and/or fluid entering the fluid storage reservoir and/or fluid exiting the fluid storage reservoir and/or any other data collected by any sensors and/or detectors and/or meters used in the system of the invention. The output system data further comprises the data collected by the marker detectors 104, 105 which comprises the amount of marker present in the fluid withdrawn from the organ and the amount of marker present in the systemic blood circulation. The detected amount of marker in the systemic blood flow provides the practitioner with an evaluation of the fluid leakage rate from the organ to the systemic blood flow. It is hence possible for the practitioner to react and intervene whenever the leakage rate is esteemed to be high and/or presenting a toxic risk for the subject. The output system data further comprises the volume of fluid present in the fluid storage container.

The input system data comprises the fluid flow rate to be withdrawn from the fluid storage reservoir 107 which is directed to the organ inflow. The input system might further comprise data collected by the different flow meters which comprises the flow rates of the fluid entering the organ, data collected by sensors for measuring the temperature of the fluid entering the organ and/or fluid exiting the fluid storage reservoir; the level of oxygen in the fluid entering the organ and/or fluid exiting the fluid storage reservoir. In a preferred embodiment, the input system data is, at least partially, manually adjusted by the practitioner. For instance, in the event that a high leakage rate of the fluid to the systemic blood circulation is observed, the practitioner can manually decrease the flow rate at which fluid is withdrawn from the fluid storage reservoir and hence the flow rate of the fluid entering the perfused organ.

In a preferred embodiment, a processing unit 112 $i$ is used for adjusting the fluid flow rate which is withdrawn from the fluid storage reservoir 107 and directed to the organ 101 inflow, said processing unit 112 $i$ is implemented with a method for receiving and processing the output system data and sending a signal to the pump 108 comprising the input system data. This allows automatisation of the perfusion, thereby considerably reducing the number of practitioners required during the perfusion. In a preferred embodiment, the method comprises an algorithm.

In a preferred embodiment, the output system data received by the processing unit 112 $i$ comprises the fluid pressure inside the organ, the fluid flow rate at which fluid is withdrawn from the organ, the amount of marker measured by the detector positioned upstream of the inlet of the fluid storage reservoir and the amount of marker measured by the detector positioned in at least one vessel of the systemic blood circulation. In addition, the output system data received by the processing unit 112 $i$ might further comprise all the data described above. In a preferred embodiment, the input system data comprises a determined fluid flow rate at which fluid is withdrawn from the fluid storage reservoir and directed to the organ inflow. The output system data further comprises the volume of fluid present in the fluid storage container. In addition, the output system data received by the processing unit 112 $i$ might further comprise all the data described above.

In a preferred embodiment, the withdrawal of fluid from the organ 101 and directing said fluid to the fluid storage reservoir 107 and the withdrawal of fluid from the fluid storage reservoir 107 and directing said fluid to the organ inflow 101 are continuously performed. In a preferred embodiment, the fluid pressure inside the organ is continuously measured.

In a preferred embodiment, the marker is selected from the group comprising radiomarkers, dyes such as Indocyanine Green, the therapeutic agent, a therapeutic agent derivative, alkaline phosphatase, 5' nucleotidase, gamma glutamyl transpeptidase, ALT, AST, PT, INR, albumin, bilirubin.

In a preferred embodiment, the method further comprises an optional washing step wherein the organ 101 is perfused using a physiologic solution wherein said solution is stored in at least one container 122. The washing step can be performed either before the perfusion with the therapeutic agent or when the perfusion of the organ with the therapeutic agent is completed. Said container might be connected to a pump 108 for the withdrawal of physiologic solution at a determined flow rate. The pump is suitable to be connected to the organ inflow. The container 122 might be connected to the inflow tubings 103 and/or to the processing unit 122 i which will send a signal to actuate a valve 121. Said valve 121 is positioned between the container 122 and the pump 108 and is used for allowing or preventing the withdrawal of the physiologic solution from said container 122. The valve can also be manually actuated by the practitioner.

In a preferred embodiment, the fluid flowing in the inflow tubings 103 is optionally passed through at least one oxygenator 110 which is positioned downstream of the outlet of the fluid storage reservoir 107.

In a preferred embodiment, the fluid flowing in the inflow tubings 103 is optionally passed through at least one heat exchanger 109 positioned downstream of the outlet of the fluid storage reservoir 107.

In a preferred embodiment, the fluid flowing in the outflow tubings 103 is optionally passed through at least one filter 106 positioned upstream of the inlet of the fluid storage reservoir 107.

It is to be understood that the fluid entering and/or exiting the organ is optionally passed through all the elements of the system described above such as the filter 106 positioned upstream of the inlet of the fluid storage reservoir 107, the injection manifold 111 for adding a marker and/or a therapeutic agent to the fluid withdrawn from the fluid storage reservoir and directed to the organ inflow and the bubble trap 112.

In a preferred embodiment, one or more third retrievable medical device is introduced used for the occlusion of the organ vessels wherein the first and/or the second medical device are not introduced. Said device is as described above for the system according to the present invention.

In a preferred embodiment, the fluid storage reservoir 107 is connected to at least one blood source 117 for adding blood to said reservoir if needed. The person skilled in the art will appreciate that the added blood is of the same type as the subject's blood.

In a preferred embodiment, the first medical device and/or the second medical device and/or the third medical device are percutaneously introduced into the different organ vessels; which is a non-invasive introduction thereby permitting repetitive perfusion of the organ.

In a preferred embodiment, the present invention allows perfusion of an isolated organ using a therapeutic agent wherein the perfusion parameters, such as flows, pressures, durations etc, are automatically adjusted. According to the invention, there is no need for a team comprising at a minimum a perfusionist, anesthesiologist and nuclear radiologists to monitor and control the perfusion. The invention reduces the number of people required and simplifies a very complicated medical procedure by using a processing unit 122 i and a computer implemented with a method to adjust the used machines, to minimize the leak rate of the perfused therapeutic agent to the systemic circulation and to automate the various processes of the perfusion.

The invention is novel as there are no real time leak tests and leak control methods and/or devices and/or systems are available today. Nowadays, to secure a minimum safety level, it is needed to inject the patient with a radioactive load, a technical specialist will continuously measure the radioactive load in the perfused organ and the systemic blood flow, evaluate the possibility of drug and isotope loaded perfusate leaking to the patients system. The technical specialist verbally warns the medical doctor in charge. The latter assigns the perfusionist to adjust the settings to get a control over the situation again or decides to start immediately a washout of the perfusate ending the procedure. The present invention provides a fast and adequate corrective action which ensures patient's safety.

In addition to fluid leakage monitoring and correction, the invention allows a continuous measurement of the perfused organ liver parameters such as flow-rates, pressures, drug regimes, additives etc. The invention allows an optimized treatment wherein real time measurements are used for an immediate reaction from the practitioner.

In the method of the invention, the blood flows into and out of the organ that is isolated. The method comprises the step of determining all major blood sources into and out of the organ. Before starting the procedure, the perfusion path must be determined. The perfusion_can take place orthograde or retrograde. Some vessels may be only occluded and not used, if desired. The perfusion path is dependent upon the organ being treated and will have to be determined prior to clinical use. The method of the invention can also be applied to open or partially open procedures especially when it is not possible to access an organ percutaneously. For percutaneous access, a vessel is located using ultrasound and accessed with a guidewire using the Seldinger technique. Once a vessel has been accessed an introducer sheath can be placed. The normal blood flow can then be controlled using occlusion balloons with central lumens for the perfusion or stent-like devices to isolate the blood flow to or from the organ from the systemic blood flow. If the blood flow is occluded, it may be desirable to shunt the blood from the systemic side back into the systemic circulation to minimize the possibility of thrombus formation. The effectiveness isolation of the vessel can be verified angiographically when possible. Once organ isolation has been verified the perfusion can start.

The method of the invention comprises the step of connecting the perfusion devices to the perfusion system and the processing unit. The perfusion system is primed with either blood or physiologic solution as needed, in order to prevent any air from entering the perfusion circuit. The perfusion system consists of at least one roller or centrifugal pump(s) that pull blood from the organ to be treated. The blood is collected into a storage reservoir. Perfusate is pumped out of the reservoir and back into the organ. Optionally, the perfusate can be pumped through a heat exchanger, to make it warmer or colder, as desired, and/or an oxygenator prior to being returned to the organ.

In the method of the invention, the intra-organ pressure can be measured through any static lumen that is in direct contact with the perfusion blood circuit. The pressure data is communicated to the processing unit as a system output data. The pumps for withdrawing fluid from the organ and for withdrawing fluid from the fluid storage reservoir are adjusted so that there is a negative balance, i.e. the flow from the organ is higher than the flow to the organ. The inventors observed, through in-vivo testing in an animal model, that if the intra-organ pressure can be reduced below the systemic pressure, the leakage from the perfusion circuit or from the organ to the systemic blood flow can be reduced or eliminated. The processing unit will adjust the flows until the desired intra-organ pressure is obtained. Once the desired intra-organ pressure is obtained, the leakage monitoring can start.

Isolation of the organ in the method of the invention can be continuously monitored several ways. First a radiomarker, such as $^{99m}$Tc, is bound to a larger molecule, such as albumin or red blood cells, in order to prevent migration through cell walls that may indicate a false leak. The radiomarker can be detected using sodium iodide (NaI) crystal scintillation counter or similar. One method of detection uses a single NaI detector placed over an area of the body that has high blood flow but is sufficiently far from the organ being perfused to prevent background noise, e.g. the groin area if treating the liver. A small amount of the radioisotope is first injected into the systemic circulation for calibration purposes. A larger amount of radioisotope, e.g. 10× the calibration dose, is then injected into the isolated organ. The NaI detector is continuously monitored by the processing unit and any leakage to the systemic circulation is minimized by adjusting the perfusion dynamics.

Another method of nuclear detection uses two NaI scintillation counters placed in-line. The detectors are housed in lead shielding to prevent the possibility of any background noise from the perfused organ. One detector is placed in line on the perfusion circuit and a second detector is placed in-line on any extracorporeal systemic shunts, e.g. a veno-venous bypass, if present. A small amount of radioisotope is injected into the systemic circulation prior to use for calibration purposes. The leakage to the systemic circulation can be detected by the detector on the systemic shunt and verified by the detector on the perfusion equipment. The advantage of this system is that there is essentially no possibility of background measurement in the systemic circulation from the organ being perfused. Additionally, the second detector on the perfusion circuit will verify the presence of a leakage to the system, the counts will decrease on the perfusion detector and the inverse will happen on the systemic detector. A variation of this setup is if there is not a systemic shunt made. In this case, the systemic detector can be placed over an area of the body that has high flow as in the first method described. The output from the detectors is monitored by the processing unit and any leakage to the systemic circulation is minimized by adjusting the perfusion dynamics.

In a preferred embodiment, once the leak rate to the systemic circulation has stabilized at an acceptably low value, the therapeutic agent is administered into the perfusion circuit. This can also be performed automatically as part of the processing unit signal. In a preferred embodiment, the uptake of the therapeutic agent can be monitored by the processing unit and the perfusion parameters adjusted to obtain the correct pharmacokinetic response.

The method of invention allows for and monitors the perfusion for a specific time period. At the end of the time period the processing unit can start a wash out procedure to remove any therapeutic agent in the perfusate. This can be done by prescribing a time and/or volume of clean blood or physiologic solution to replace the perfusate or by another method known to the person skilled in the art, depending on the application. After the therapeutic agent has been removed from the perfusate, the perfusion equipment is disconnected from the isolation medical devices. Said devices are then retrieved and normal blood flow is restored to the patient. All access sites are closed and the procedure is completed.

FIG. 14 illustrates an example for perfusing an organ 101 using the system and/or the method and/or the computer implemented method according to the present invention. Once the organ has been isolated using percutaneous interventional techniques, the isolation catheters are attached to the outflow tubing 102 and inflow tubing 103 of the system. Prior to connecting the devices to the system, the isolation of the organ has been verified angiographically. The perfusion is primed with blood or physiologic solution as desired prior to use.

Blood is pumped from the organ using pumps 104 and 105. The number and type of pumps required is dependent upon the organ being treated. The pumps can be either roller pumps which is flow controlled, or centrifugal pumps which are pressure controlled. The purpose of pumps 104 and 105 are to pull blood from the organ, or create suction from the organ. It is also possible for a single pump to pull blood from several different vessels, as desired by the clinician. The blood that is pulled from the organ can then be run through a blood filter 106 if desired. This filter is used to remove any bubbles or micro emboli that may be present in the blood. In a preferred embodiment, the filter is provided with a reservoir which serves as a buffer of perfusate for the fluid storage reservoir 107. The filtered blood is then collected in the fluid storage reservoir 107. Blood from the reservoir 107 is pumped into an optional heat exchanger 109 and oxygenator 110. The need for hypo or hyperthermia and oxygenated blood is based on the requirements of the medical treatment and application and may not always be necessary. Similar to the outlet pumps, more than one pump 108 can be used to return blood to the organ if desired. This pump is preferably a roller pump, but a centrifugal pump may be better for some applications. From the oxygenator, the blood then flows through an injection manifold 111 and bubble trap 112. The injection manifold can be connected to syringe pumps as needed to administer at least one marker and at least one therapeutic agent e.g. chemotherapy or heparin, as needed. The syringe pumps connected to the manifold 111 can be controlled by the processing unit 112 i to administer the therapeutic agent at predefined points or as a result of continuous blood monitoring. From here the blood is returned to the organ.

The method of the invention also allows for various sensors, valves, metering pumps, or flow meters 113, 114, 115, 116 to be placed on the outflow tubings and/or the inflow tubings. This allows to monitor and control the fluid flow as desired by the processing unit. The level of fluid in the reservoir 107 is also monitored by the processing unit. Fluid and can be added from a blood source 117 if the level gets too low. There is an overflow exit 118 on the reservoir that can collect excess perfusate, if necessary, for example during the washout step.

Detectors 119 and 120 can be placed on the perfusion circuit and the systemic circulation. Ideally both detectors are housed in lead shielding with the perfusion line to avoid any background interference. This will only be possible in the systemic circulation if there is an extracorporeal shunt made e.g. a veno-venous bypass. If there is no shunt, detector 120 is located over an area of the body with high blood flow that is sufficiently far away from the organ being treated to prevent interference. The processing unit can control the administration of radioisotope and perform all the leak rate calculations.

The control unit also called processing unit, 112 i is where the method is implemented. Said method comprises a programmed algorithm. The processing unit is provided with a graphical interface for the user. In order to control the method of the invention, the user will be required to input critical information. Such information may be: target perfusion flow rate, acceptable flow range, and maximum leak rate and perfusion time. The processing unit can use feedback loops to control the pump speeds to obtain the desired intra-organ pressures and leak rates. Additionally, the processing unit will automate the steps of the perfusion as follows: first the flow rate into and out of the organ will be increased until the target flow rate is obtained. During this procedure, the flow meters 113, 114, 115 and 116 can be read to assure that the inflow and/or outflow tubings has not collapsed or the flow has not been compromised. During in-vivo animal testing, monitoring the perfusion tubings for adequate flow consumed a lot of time. If there is a problem with the flow, the practitioner will be notified so that the problem may be corrected. Once the flow is acceptable the processing unit will begin the process of lowering the intra-organ pressure to the targeted value. This is done by adjusting the negative balance of the perfusion pumps. This can be done using a feedback controller e.g. a PID controller. During this time the patency of all perfusion lumens is verified by flow meters. The processing unit can then start the leakage monitoring by administering the marker and controlling the leak rate as was previously described. At the end of the perfusion period, the processing unit can actuate valve 121 and rinse the organ with clean blood and/or physiologic solution 122. The invention also allows for the connection of other sensors, actuators or pumps as needed 124. Such sensors might be used for conducting in-process assays to determine drug concentrations or for blood analysis as needed.

Organs can be isolated and perfused using the first, second and third medical devices as described above. To control a local, isolated, perfusion or infusion procedure it is however necessary to deal with patient specific vasculature, collateral connections, to control the communication between the perfusion or infusion liquid and the patients system.

In a third aspect, the present invention provides a computer implemented with a method for the monitoring and the control of a subject's organ perfusion system, said system comprises at least one pressure detector for measuring fluid pressure inside the organ, outflow tubings for withdrawing fluid from said organ and inflow tubings for delivering fluid to the organ, wherein the method comprises the steps of:
  receiving output system data from the system whereby the output system data comprises the fluid pressure inside the organ, a fluid flow rate at which fluid is withdrawn from the organ, an amount of a marker present in the fluid flowing in the outflow tubings, the amount of marker present in the systemic blood flow of the subject,
  processing the received output system data, and
  sending input system data whereby said data comprises a determined fluid flow rate at which fluid is delivered to the organ through the inflow tubings of the system.

Figure 15:
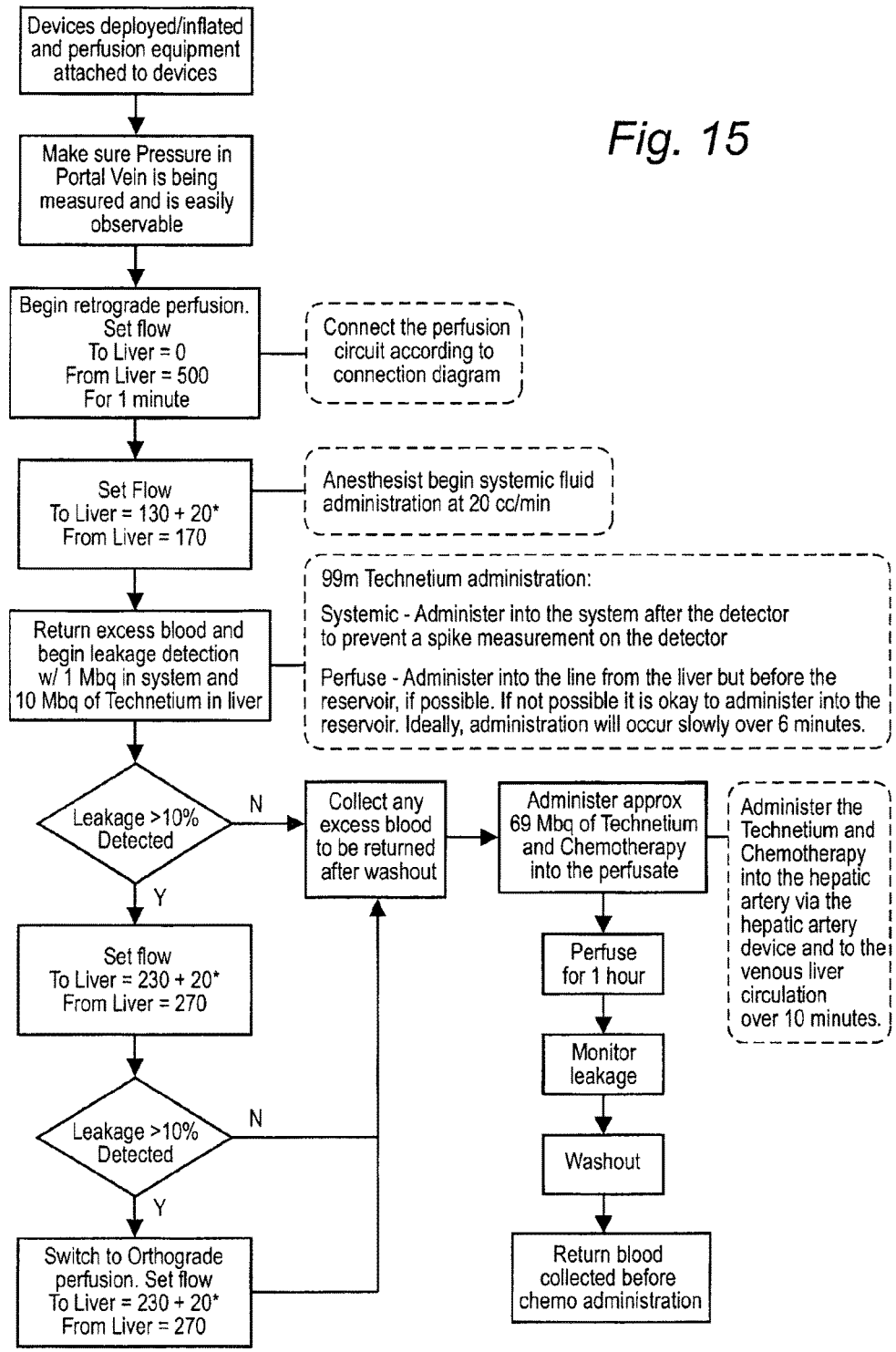
FIG. 15 is a flowchart of an algorithm of the processing unit that can be used to control the perfusion system of FIG. 14.
Figure 16:
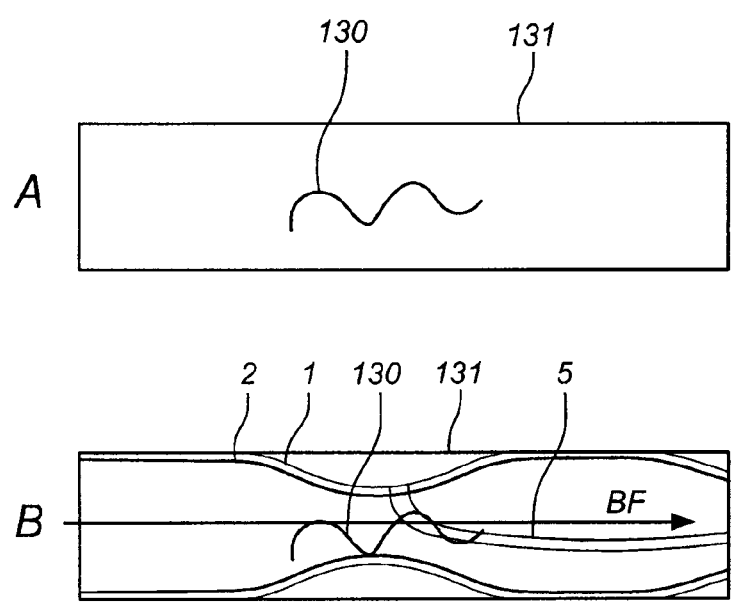
FIG. 16A shows a vessel having a lesion
FIG. 16B shows the second retrievable medical device introduced in the vessel having a lesion.

FIG. 15 illustrates an exemplary flowchart of a method and/or an algorithm that can be implemented to the computer and used to control the perfusion of liver using a system and/or a method according to the present invention. The flowchart describes the different steps of the method that have to be performed after isolating the liver using the first, second and the third medical devices as described above. N and Y in the figure respectively refer to "No" and "Yes".

It is to be understood that all the values of FIG. 15 are exemplary values and can be modified according to the organ to be pefused and to the disease to be treated. In FIG. 15, the star indicates that the values represented therein are exemplary values. At the start of the retrograde perfusion, the fluid flow rate to the liver is set a 0. The fluid flow rate withdrawal from the liver is set at a value of from 200 to 1000 cc/min, preferably of from 300 to 800 cc/min, more preferably from 400 to 700 cc/min, most preferably about 500 cc/min. Said withdrawal is maintained for a period of from 20 sec to 5 min, preferably from 30 sec to 3 min, more preferably from 40 sec to 2 min, most preferably about 1 min.

Afterwards, the fluid flow rate to the liver is set at a value of from 20 to 200 cc/min, preferably from 50 to 150 cc/min, more preferably from 70 to 140 cc/min, even more preferably from 80 to 120 cc/min, most preferably about 100 cc/min. The fluid flow rate withdrawal from the liver is set at a value of from 100 to 250 cc/min, preferably of from 120 to 220 cc/min, more preferably of from 150 to 200 cc/min, most preferably about 170 cc/min.

In a preferred embodiment, the blood loss of the method according to the present invention is not more than 2 liters, preferably not more than 1 liter. The blood loss is at most 300 cc, preferably at most 250 cc, more preferably at most 200 cc, even more preferably at most 150 cc preferably, most preferably at most 100 cc. In a further preferred embodiment, the blood loss is at most 50 cc, preferably at most 40 cc, more preferably at most 30 cc, even more preferably at most 10 cc preferably, most preferably there is no blood loss using the method according to the present invention. By blood loss it is referred to the volume of blood containing the therapeutic agent and/or any derivative of said agent which is not returned to the systemiuc blood flow at the end of the perfusion procedure and before the retrieval of the introduced medical devices.

The present invention provides an auto-controlled optimal perfusion flow wherein a local treatment is optimized in relation to organ isolation and a controlled auto stop when the measured or calculated leak is higher than a preset value. This preset value could be for instance a percentage of the maximum systemic allowed dose. The total leakage should be limited assuring that with the leakage, the maximum allowed systemic dose remains below the defined maximum values, preferable <40% of the systemic allowed maximum, more preferable <10%.

In a fourth aspect, the present invention provides for the use of a system as described above, for the monitoring and the control of a subject's organ perfusion.

In a fifth aspect, the present invention provides for the use of a method as described above, for the monitoring and the control of a subject's organ perfusion.

In a sixth aspect, the present invention provides for the use of a computer implemented with a method as described above, for the monitoring and the control of a subject's organ perfusion.

Therapeutic Agent

The therapeutic agent of the kit according to the present invention can be a treatment fluid or particles or beads containing said treatment. Particles are known for the person skilled in the art and for instance described in US2004/197264, the content of which is incorporated herein by reference. The particles comprise a material selected from the group consisting of glass, polymer and resin; a first radioisotope that emits a therapeutic [beta]-particle; and a second radioisotope that emits a diagnostic [gamma]-ray; wherein the atomic number of the first radioisotope is not the same as the atomic number of the second radioisotope. In a preferred embodiment of the present invention, the particles are beads comprising a radioactive element, preferably polymer or glass beads.

The particles are used to treat organ tumors. The particles are delivered into the organ blood flow through an artery of the organ to be treated. The radioactive particles are selectively implanted in the microvascular supply of the tumor wherein they become trapped. The particles emit beta radiation for a certain period of time which will kill the tumor.

The particles might be used to treat liver cancer for instance. Patients with primary or metastatic tumors can be treated by radio-embolization via a catheter which tip is placed in the hepatic artery. A direct injection of beads into the tumor is also possible using a needle. The spheres eventually lodge in the microvasculature of the liver and tumor, remaining until the complete decay of the radioisotope.

The diameter of said particles is in the range from about 1-500 micrometers, preferably 2-400 micrometers, more preferably 4-300 micrometers, most preferably 5-200 micrometers. The diameter of said particles can be any value comprised within the mentioned ranges.

In a further preferred embodiment, the size of the particles is comprised between 10 and 300 micrometers, preferably between 15 and 200 micrometers, more preferably between 20 and 60 micrometers, most preferably the particles size is around 30 micrometers.

Preferably the diameter of said particles is comprises between 50 and 70 micrometers, more preferably between 40 and 60 micrometers, most preferably around 30 micrometers.

First Retrievable Medical Device

The first medical device is used for the simultaneous or the separate perfusion and occlusion of the vessel of the organ inflow. Said device comprises a body having a distal end, a proximal end, at least one lumen extending between the proximal end and the distal end, at least one opening which is in fluid communication with the lumen for delivering a fluid to said vessel and at least one expandable balloon coupled with the body of the device.

The first retrievable medical device (26, FIG. 4) is preferably a catheter. For liver tumor treatment, said catheter will be introduced in the hepatic artery (HA). The insertion of said catheter occurs via the right femoralis artery into the hepatic communis artery.

In a preferred embodiment, the first medical device (26, FIG. 4) allows shunt debits in the range of 10-500 cc/min allowing slow supply of agents with unwanted tissue reactions, like spasms, and higher flows for bolus treatments.

In a preferred embodiment, the first medical device has a small size and is a flexible device such as it can be positioned following torturous pathways. The diameter of said device is comprised between 5 F (=about 1.67 mm) and 7 F (=about 2.3 mm). The length of the device is around 800 mm. The latter allows the positioning of the device close to, or in, an organ. The device provides for the control of the blood flow through the targeted organ and provides a non-limited infusion/perfusion debit.

The device is shown in FIG. 11A and comprises a grip area 67, a single lumen 66 and at least one balloon 65. The expansion of the balloon is induced and controlled by the infusion/perfusion liquid. The device can occlude, at least partly and/or temporarily, the vessel to control the blood flow and to inject a therapeutic agent into that organ in flow rates of at least 20 ml/min. In a preferred embodiment, the balloon of the first medical device is provided with an interior which is in fluid communication an inflation lumen through at least one opening positioned in the body of the device. During delivery of the therapeutic agent into the vessel, the infusion/perfusion liquid containing said therapeutic agent flow in the lumen 66 and inflates the balloon 65 by flowing through the openings 68 and 69 (FIG. 11 A). FIG. 11B shows another embodiment of the catheter wherein the openings 70' allows the flow of the infusion/perfusion liquid leading to the expansion of the balloon 70.

Figure 11C:
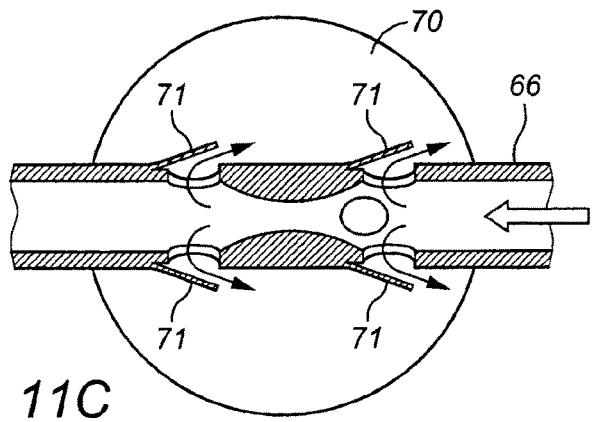
FIG. 11C, FIG. 11D and FIG. 11E illustrate an embodiment of the first medical device wherein each opening allowing fluid communication of the lumen with the interior of the balloon is provided with a valve.
Figure 11D:
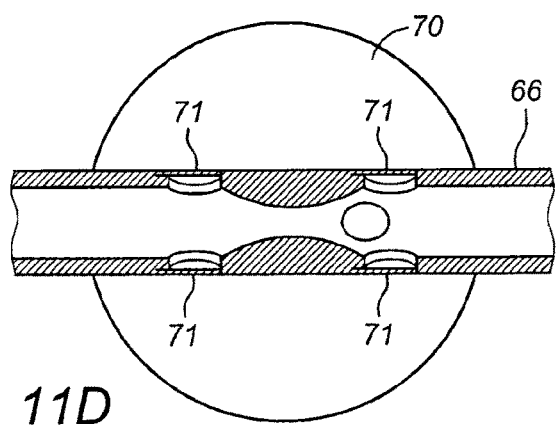
Figure 11E:
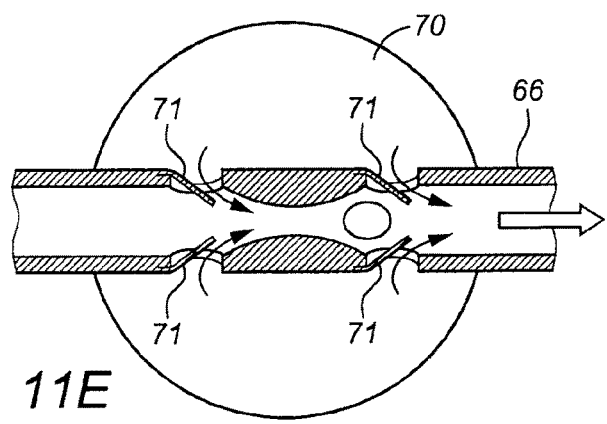

The device can be further provided with a plurality of valves 71 as shown in FIGS. 11C, 11D and 11E. Said valves 71 are located on the surface of the openings. When the perfusion liquid is injected a pressure in created in the lumen of the device. Said liquid opens the valves 71 and accumulates in the balloon 70 thereby inflating it as illustrated by the arrows in FIG. 11C. When the injection of the perfusion liquid is terminated the valves 71 close and the balloon remains in an inflated state (FIG. 11D). When the device is to be retrieved at the end of the treatment, a negative pressure is created inside the lumen of the device which leads to the opening of the valves 71 inside the lumen and to the deflation of the balloon 70 (FIG. 11E). The valves are made of any suitable flexible material such as but not limited to silicon. A pull can be provided in the device to control the opening and closing of the valves.

FIG. 12A shows the catheter of the first medical device when the balloon 81 is not in an expanded state. The lumen 80 diameter is reduced at one end 82 of the catheter. The narrowed end can be provided with a conical tip. Reducing the diameter at one end of the catheter leads to a pressure increase during the perfusion and/or delivery of the therapeutic agent. The latter accelerates the expansion of the balloon. The diameter reduction ensures that the balloon segment will expand at minimal defined flows. The diameter at the end 82 of the catheter is reduced by at least 10%, 20%, 30%, 40%, 50%, 60%, 70%, 80%, 90% or any value comprised between these values, compared to the diameter of the lumen to assure the expansion of the balloon during perfusion. FIG. 12B shows the catheter when the balloon 81 is in an expanded state due to the flow of the infusion/ perfusion liquid in the lumen 80. Said infusion/perfusion liquid creates a pressure inside the lumen due to the reduced diameter of the catheter end. Said fluid and fluid pressure leads to the inflation of the balloon 81.

The catheter of the first medical device is made of a biocompatible materials generally applied for short term (<120 minutes) endovascular procedures. The balloon 81 can be the most flexible part of the catheter, for instance by having smaller wall thickness, or made from other materials bonded to the catheter. The catheter of the first medical device according to the present invention is a percutaneous device having a minimum quantity of material to ensure the vessel occlusion, and to increase the flexibility and maximize the infusion/perfusion flow.

Figure 8:
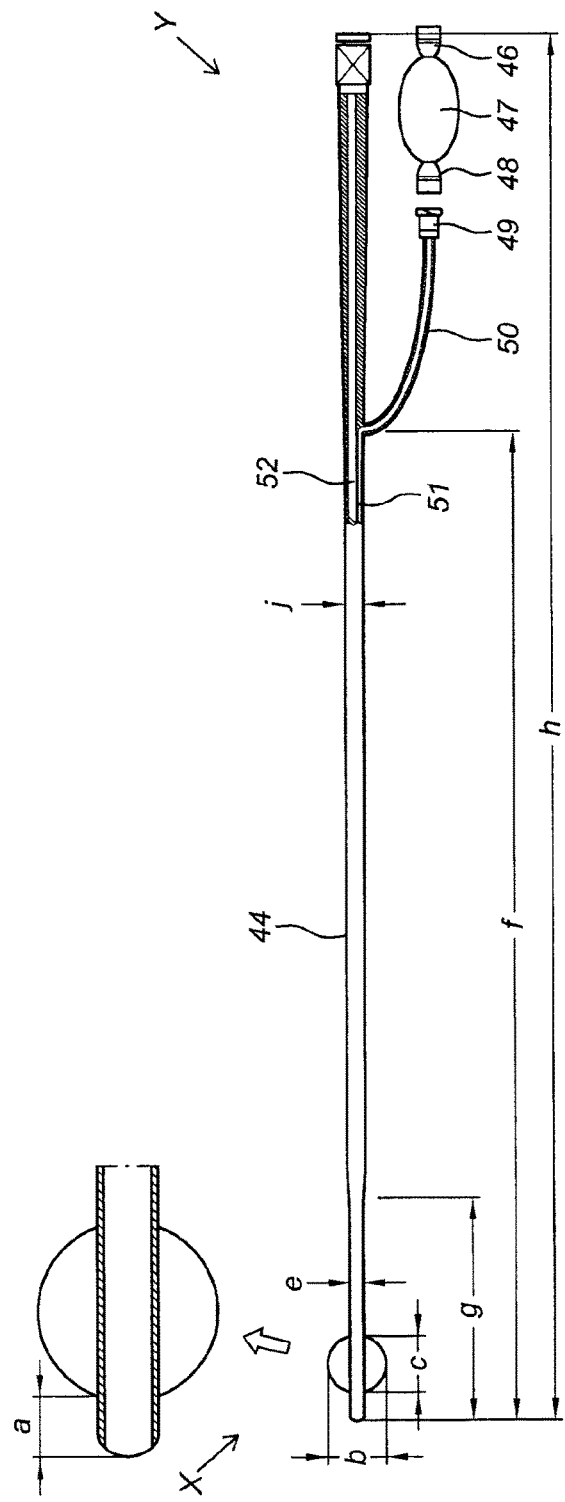
FIG. 8 detailed schematic illustration of the first medical device.

FIG. 8 shows the catheter having a guide wire 52 and a lumen 51. The balloon is substantially spherical and is positioned at the distal end X of the device. The length c of the expanded balloon is about 10 mm. The catheter comprises a tube 44 having a lumen. The diameter j of said tube 44 is about 2.5 mm. The diameter e of distal end X portion of the first retrievable medical device is about 2 mm said portion extends over a length g of about 150 mm. The length h of the catheter is about 900 mm. The tube 44 is provided at the proximal end Y with a female luer adapter 49. At the distal end X, the tube 44 is provided with a balloon that inflates when the user pushes the inflation bladder 47. The latter is provided with an inflation check valve 46 and a male luer adapter 48. The inflation bladder 47 is connected to the catheter via a female luer adapter 49 and a connector tube 50.

Second Retrievable Medical Device

The second retrievable medical device is used for isolating and collecting the organ outflow. Said device is provided with a distal end and a proximal end; said second medical device comprises a catheter suitable for deploying an expanding member; the proximal end of the expanding member is attached to the distal end of the catheter. In a preferred embodiment, the expanding member of the second retrievable medical device comprises a carrier and an impermeable liner which is bonded to at least a part of the carrier length. In a further preferred embodiment, the expanding member of the second medical device has a tubular shape. In another preferred embodiment, the expanding member of the second medical device has a bell shape.

In a preferred embodiment of the present invention, the expanding member of the second medical device comprises a liquid permeable carrier configured to adopt an essentially cylindrical state when compressed, and to expand radially to form a central part flanked by two annular ridges.

FIG. 1 illustrates an embodiment of the second medical device according to the present invention. The device comprises a radially, self-expandable tubular member 9, shown in the expanded state attached to a delivery catheter 10. FIG. 1A shows a transverse cross-section of the catheter. Said expandable tubular member 9 can be a self-expandable tubular member 9.

The second medical device is provided with a distal 21 and a proximal 20 end, comprising a hollow, self-expanding tubular member 9 and a catheter 10 suitable for deploying a self-expanding tubular member 9, wherein:
 the tubular member 9 is configured to expand radially to form a central part 11 flanked by two annular ridges a distal annular ridge 12 and a proximal annular ridge 13,
 the tubular member 9 comprises a liquid-impermeable area, defined at least by the region flanked by the annular ridges 12,13,
 the tubular member 9 comprises two liquid-permeable regions, one distal to the distal annular ridge 12 and one proximal to the proximal annular ridge 13, so forming a passageway 14 between the distal end 21 and the proximal end 20 of the tubular member 9 for the flow of vessel fluid,
 the proximal end 20 of the tubular member 9 is attached to the distal end 21 of the delivery catheter 10,
 the liquid impermeable area is disposed with one or more fluid ports 15 for blood passage.

The self-expandable tubular member 9, known herein as 'tubular member', is typically an elastic tube that self-expands after having been compacted. Illustrative examples of self-expandable tubular members are disclosed in the following documents all of which are incorporated herein by reference: U.S. Pat. No. 5,876,445, U.S. Pat. No. 5,366,504, U.S. Pat. No. 5,234,457, U.S. Pat. No. 5,061,275; Watkinson et al: The role of self-expanding metallic endoprostheses in esophageal structures, "Seminars in Interventional Radiology", 13(1):17-26 (March 1996). In a further preferred embodiment, the carrier is made of a braided wire mesh. The annular ridges are suitable to contact the vessel of the organ thereby apply a sealing pressure to the vessel wall.

In a preferred embodiment, the tubular member 9 comprises, in the expanded state, a central part 11 flanked by two annular ridges—a proximal annular ridge 13 and a distal annular ridge 12. The central part 11 radially expands to a lesser degree compared to the annular ridges 12, 13. The expanded central part 11 typically has a cylindrical shape while the annular ridges 12, 13 are at least partly conical, so forming a funnel-like structure in the expanded state. By designing the device as such, it is formed partly as an hour-glass or dumb-bell upon expansion. When deployed in a bodily vessel, the central part 11 forms an annular lumen 18, sealed by the annular ridges 12, 13 for the collection of blood brought to said bodily vessel by other vessels, such as collateral vessels.

The skilled person will appreciate the diameters of the tubular member 9 at the annular ridges 12, 13 and central part 11 in the expanded state may be adapted according to the diameter of the vessel at the deployment site. The diameter of the central part 11 should be wide enough to avoid obstruction of blood flow, but not too wide that flow reaches high levels that will affect leakage resistance and disturb laminar flow. The diameter of the annular ridges 12, 13 should be selected such as to provide a perfect sealing against the vessel's inner wall when the tubular member 9 is in the expended state. The sealing is assured by the pressure applied by the carrier 2 on the vessel's wall and by the fact that the annular ridges 12, 13 contact the inner vessel over a distance comprised between 15 and 100 mm, preferably between 16 and 80 mm, more preferably between 17 and 60 mm, most preferably between 18 and 40 mm.

In another preferred embodiment, in the expanded state the central part and the annular ridges of the tubular member are designed to expand radially with the same degree. The expanded tubular member has then a cylindrical shape (FIG. 1C) with at least partly conical extremities, so forming a funnel-like structure in the expanded state. The cylindrical shape is obtained by the expansion of the carrier 2. A liner 1 having an hour-glass or dumb-bell shape is at least partly attached to the inner walls of the carrier 2 as shown in FIG. 1C. When deployed in a bodily vessel, liner 1 forms an annular lumen 18, for the collection of blood brought to said bodily vessel by other vessels, such as collateral vessels. The straight carrier 2 is made of flexible material such as braided wire mesh. Hence, it is able to follow the vessel curvatures and assure a reliable isolation between the systemic blood flow and the fluid flowing in through both the inner tube 5 and the annular lumen 18. The continuous cylindrical carrier assures an optimal opening of the vessel during the organ treatment.

Figure 1D:
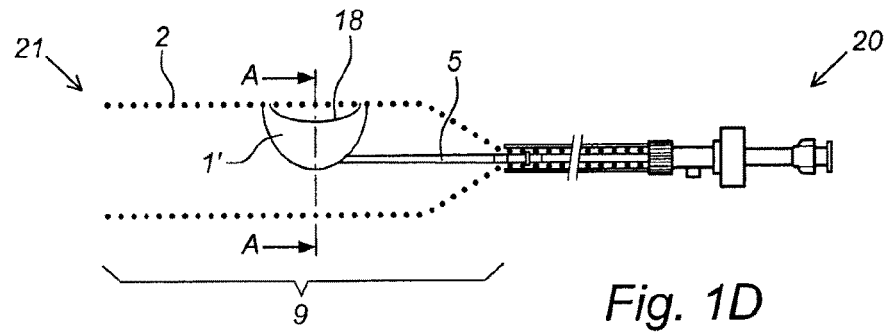
FIG. 1D illustrates a side view of another embodiment of the second medical device of the present invention wherein the distal end of the inner tube have a cup or a spoon shape
Figure 1E:
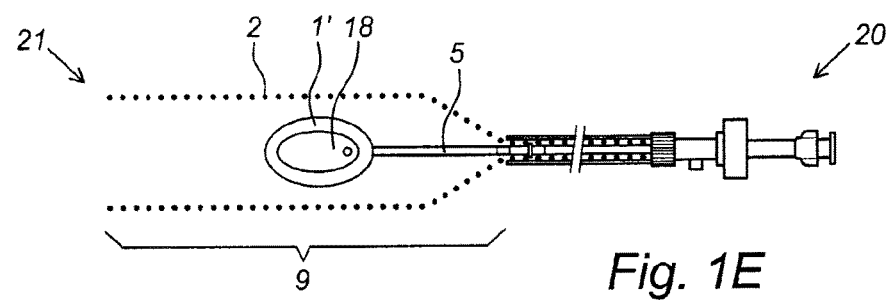
FIG. 1E illustrates a top view of the same embodiment
Figure 1F:
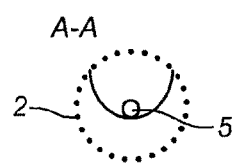
FIG. 1F illustrates a cross-section view along A-A shown in FIG. 1D.

In another preferred embodiment, in the expanded state the central part and the annular ridges of the tubular member are designed to expand radially with the same degree. The expanded tubular member has then a cylindrical shape (FIG. 1D and FIG. 1E) with at least partly conical extremities, so forming a funnel-like structure in the expanded state. The cylindrical shape is obtained by the expansion of the carrier 2. The distal end 21 of the inner tube 5 is formed as a cup or a spoon 1' which is attached in at least two locations to the carrier 2 such as to form an annular lumen 18 as shown in FIG. 1D. The cup or a spoon 1' of the device is suitable to be in fluid connection with several veins. For instance when the device is placed in the thoracic arch, the cup or a spoon 1' is suitable to be in fluid connection with several bronchial branches. FIG. 1F shows a cross sectional view along A-A shown in FIG. 1D while FIG. 1E shows a top view of the second medical device according to the present embodiment. The straight carrier 2 is made of flexible material such as braided wire mesh. Hence, it is able to follow the vessel curvatures and assure a reliable isolation between the systemic blood flow and the fluid flowing in through both the inner tube 5 and the annular lumen 18. The continuous cylindrical carrier assures an optimal opening of the vessel during the organ treatment.

Figure 1G:
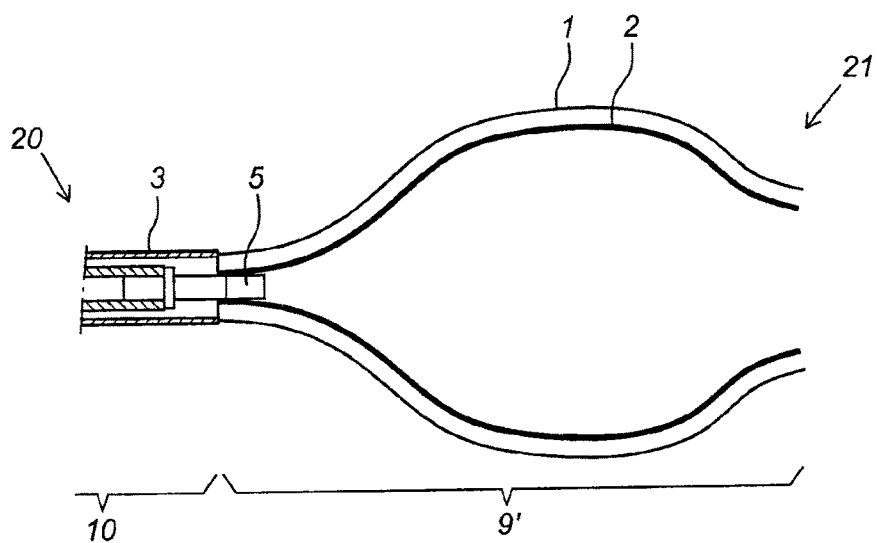
FIG. 1G illustrates another embodiment of the second medical device of the present invention in the expanded state wherein the device has a bell shape.

In another preferred embodiment, the second medical device in expanded state has a bell shaped member 9' as shown in FIG. 1G. Said bell shaped member 9' can be a self expanding bell shaped member. The device comprises a carrier 2 and liner 1 which is disposed at the outer wall of the carrier 2. The liner 1 is in this embodiment provided over the full length of the device as shown in FIG. 1. G. The device is mainly used for delivering a therapeutic agent to an organ. The therapeutic agent flows through the inner tube 5.

It is to be understood that all the embodiments of the second medical device described above can be used for delivering a therapeutic agent to an organ and/or retrieving a therapeutic agent from an organ. The delivery and/or retrieval of the therapeutic agent are performed while maintaining the systemic blood flow of the patient. The treated organ is for example liver or lungs.

For liver treatment, the second medical device is positioned in the vena cava with the proximal extremity just above the inflow of the renal veins. The proximal part of the device occludes collateral inflow form renal veins up to the annular lumen 18 around the hepatic veins. This isolation is assured by an annular ridge that is rounded at the end, preventing possible damage of the entrance of the right atrium even when placed deep into the right atrium.

The annular lumen 18 around the hepatic veins is about 15-20 mm long. The practitioner will not encounter difficulties to position the device in front of the hepatic veins. With exception of the annular lumen 18, the vena cava is in contact with the second medical device: from renal veins up to right atrium.

The minimum diameter of the central part 11 in the expanded state may be 45, 50, 55, 60, 65, 70, 76, 80, 85, 90, or 95% of the internal diameter of the vena cava, or a value between any two of the aforementioned values. Preferably the minimum diameter of the central part 11 in the expanded state is at least 50% of internal diameter of the vena cava. According to one aspect of the invention, the minimum diameter of the central part 11 in the expanded state is between 6, 8, 10, 12, 14, 16, 18, 20, 22 mm or a value in the range between any two of the aforementioned values, preferably 8 to 18 mm diameter.

The maximum diameter of the annular ridges 12,13 in the expanded state may be 5, 10, 15, 20, 25, 30, or 35% larger than the internal diameter of the vena cava, or a value between any two of the aforementioned values. Preferably the maximum diameter of the annular ridges 12,13 in the expanded state is between 10, 15, 20, 25, 30% larger than internal diameter of the vena cava. According to one aspect of the invention, the maximum diameter of the annular ridges 12,13 in the expanded state is between 20, 25, 30, 35, 40, 45 mm or a value in the range between any two of the aforementioned values, preferably 20, 26, 33 or 43 mm diameter.

According to one aspect of the invention, the difference between the maximum diameters of the annular ridges 12, 13 and the minimum diameter of the central part 11 in the expanded state may be 2, 3, 4, 5 or 6 mm or a value in the range between any two of the aforementioned values, preferably 4 to 5 mm diameter.

The region flanked by the annular ridges 12, 13 defines a liquid impermeable area. The skilled person will understand the adaptations to the tubular member 9 necessary to define a liquid-impermeable area that provide sealed annular lumen 18 in the deployed state. Generally, the liquid-impermeable area will extend between the annular ridges 12, 13, from the region of maximum diameter of the proximal annular ridge 13 to the region of maximum diameter of the distal annular ridge 12. It is within the practices of the skilled person to determine a lesser or greater area, for example, depending on the patency of the vessel wall.

Through the inner part of the tubular member extends a passageway 14 between the distal end 21 and the proximal end 20 of the tubular member 9; blood is able to flow there between. The tubular member 9 comprises two liquid-permeable areas, one distal to the distal annular ridge 12 and one proximal to the proximal annular ridge 13, so blood can flow from through the passageway from the distal end 21 and the proximal end 20 or vice versa. Preferably, the liquid-permeable region of the distal end 21 of the tubular member 9 comprises an open-mouthed region, while the liquid-permeable region of the proximal end 20 comprises a region 16 devoid of liquid-impermeable lining. According to one aspect of the invention the tubular member 9 comprises a carrier 2 and a liquid-impermeable liner 1. The carrier part 2 is typically, though not always, the outmost part of the device, and contacts the vessel wall in the deployed state. The carrier 2 expands in the manner mentioned above. The carrier 2 is preferably retractable which means that it normally adopts the hour-glass or dumb-bell shape mentioned above; when retracted into a cylindrical sheath, the carrier can be compressed to adopt an essentially cylindrical state, suitable for introduction into and freely positioning within a vessel. The carrier 2 can be described as being self-expanding. The carrier is attached to the catheter, to a pusher means 23 element therein described below. Preferably, the proximal end 20 of the carrier 2 is attached circumferentially to the distal end 21 of the pusher means 23, so giving the proximal end 20 of the tubular member 9 a conical shape 16.

The tubular member 9 or carrier 2 is attached to the catheter 10 or pusher means 23. It is configured to remain attached when the tubular member 9 or carrier 2 is in the retracted and deployed position. According to one aspect of the invention, it is non-releasably attached, meaning that the tubular member 9 or carrier 2 cannot be released, in situ, from the catheter 10 or pusher means 23. In other words, the device may be devoid of a mechanism for releasing the tubular member in situ. This feature allows the tubular member to be withdrawn at the same time as the catheter 10, without the possibility of leaving the tubular member in the vessel. A non-releasable attachment may still allow the member 9 or carrier 2, to be unattached from catheter 10 or pusher means 23 outside by the body, for example, using a screw fitting, a clip, a push fitting or any other secure coupling. A non-releasable attachment would also include the possibility that the member 9 or carrier 2, is permanently attached to the catheter 10 or pusher means 23.

In the expanded state, the carrier 2 is able to retain its shape without the requirement for an additional source of pressure, for example, from a balloon catheter. The carrier 2 may or may not maintain an essentially constant axial length in the compressed state compared with the expanded state.

The carrier part 2 is preferably made of a braided wire mesh, woven so as to self-expand radially. In an embodiment, the carrier is made from a surgical wire preferably of an alloy comprising Cobalt, Chromium, Nickel, Molybdenum and Iron, and more preferably a surgical wire in accordance to the standard ASTM F 1058. Alternatively, the carrier part 2 may be a knitted mesh of nitinol wire flexible in both the radial and longitudinal axes. Alternatively, other materials, such as shape memory alloy or synthetic material, can be used to produce the carrier. The carrier part 2 may, alternatively, be laser cut. The shape of the central part 11 may be formed by using crimping or heat treatment. The carrier may show a high degree of flexibility and a radial force that assures a good contact with the vessel wall after positioning. The carrier part 2 is liquid permeable, which means that blood can flow there trough, without substantial hindrance. This is achieved in the carrier because it is formed from an open wire structure and may comprise an open mouthed end. A liquid permeable region may comprise one or more openings, at least wide enough to avoid capillary action though the opening.

Because the carrier part 2 is preferably formed from an open mesh structure, it contacts the vessel wall securely in the expanded state, owing to the open structure, creating a plurality of friction points. In an expanded state, the device is securely anchored and provides strong sealing against the vessel wall. There is no requirement for applying additional pressure to the vessel walls, for example, from a balloon.

Another component of the tubular member 9 is the liner 1, which is made from a liquid-impermeable material. This is typically attached partly to the walls of the carrier 2, inside or outside the passageway lumen 14 of the device. The liner 1 is disposed at least in the region of the annular lumen 18, so that the passageway lumen 14 is liquid-sealed from the annular lumen 18 in the deployed state. Preferably the liner 1 is disposed in an area defined at least by the region flanked by the annular ridges 12, 13.

The liner 1 may be made from a biocompatible material, preferentially a medical grade expandable material e.g. an elastic material which can expand at the same time as the carrier 2. The liner may be made from a medical grade polycarbonate polyurethane formulation. The liner may, alternatively, be made from ploytetrafluoroethylene, polyurethane, silicone or polyethylene terephthalate polymers. The most preferred materials are indicated in table 2 below:

TABLE 2

Examples of preferred liner materials for use in the present invention.
All brand names are registered trademarks.

| | Supplier | Brand name | Elastomer |
|---|---|---|---|
| 1 | Polymer Technology group Inc, Berkeley CA, USA (Licensed by Boston scientific) | Bionate (Corethane) | Thermoplastic Polycarbonate Urethane |
| 2 | B.F Goodrich, Cleveland OH, USA | Estane | Thermoplastic Polyesther Urethane |
| 3 | Thermedics Inc, Woburn MA, USA | Tecoflex | Thermoplastic Polyether Urethane |
| 4 | CT Biomaterials, Woburn USA | Chronoflex | Thermoplastic Aromatic Polycarbonate Polyurethane |
| 5 | Aortech, Sidney, Aus | Elasteon | Siloxane based Macrodiol Aromatic Polyurethane |

The liner 1 may be attached to the carrier 2 by chemical or thermal bonding. The liquid-impermeable area formed by the liner 1 is disposed with one or more fluid ports 15 for blood passage; this is described in more detail further below.

Through the inner part of the tubular member 9 extends a passageway 14 between the distal end 21 and the proximal end 20 of the tubular member 9; blood is able to flow there between. The tubular member 9 comprises at least two liquid-permeable areas, one distal to the distal annular ridge 12 and one proximal to the proximal annular ridge 13, so fluid can flow from through the passageway 14 from the distal end 21 and the proximal end 20 or vice versa. A flow is indicated by arrows 'b' in FIG. 1. The skilled person will realize that liquid permeable areas should not extend into the liquid impermeable region so that the seal of the annular lumen 18 is breached. Preferably, the distal end 21 of the tubular member is open-mouthed, while the proximal end 20 is closed but is disposed with a liquid-permeable region 16 i.e. a region devoid of liner 1.

According to one aspect of the invention, a region of the carrier 16 towards the proximal end 20 of the proximal annular ridge 13, is devoid of liner 1. According to another aspect of the invention, at least part of the carrier 2 between the distal end 21 of the catheter 10 and proximal end 20 of the proximal annular ridge 13 is devoid of liner 1. This creates a large liquid passageway 14 inside the tubular member 9 while the catheter 10 is still attached. This configuration has advantages over conventional designs which employ openings and lumens within the narrow confines of the catheter tube to maintain the flow of blood. Conventional lumens are narrow bore, and can cause the buildup of pressure towards the proximal side of the occlusion device. Known devices thus require catheter tubing having larger diameters to accommodate wider a blood lumen, which catheters can then be difficult to navigate along a tortuous path of a blood vessel for example. The present device, by contrast, dispenses with a catheter blood lumen, and maintains blood flow using a wide bore passageway in the expanding tubular member 9, and with a narrow diameter catheter.

The catheter 10 part of the device is used to introduce and guide the tubular member 9 into the body vessel. The catheter 10 is also used to restrain, temporarily, the tubular member 9 in a compressed state at the distal end of the catheter. It is also used to withdraw liquid to from the annular lumen 18. In use, the catheter is introduced to a desired site within a body vessel, the restraint is removed, thereby allowing the tubular member 9 to expand by its own elastic and apply sealing pressure to the vessel wall using the annular ridges 12, 13.

Examples of delivery systems for expandable tubular members are described in the following US patents which are all incorporated herein by reference: U.S. Pat. No. 5,484,444, U.S. Pat. No. 4,990,151, and U.S. Pat. No. 4,732,152.

According to one embodiment of the invention, the catheter 10 comprises an outer tubing 3, pusher means 23 for deployment of the tubular member 9, and an inner tube 5, which extend along the length of the catheter. The pusher means 23 may be a pusher rod (or stick) 4 at least partly co-axially or concentrically disposed around the inner tube 5 (FIG. 1A). Alternatively, the pusher means 23 may be formed from the wall of the inner tube 5 (FIG. 1B).

The outer tubing 3 may be coaxially or concentrically disposed around the pusher rod 4. Where the pusher means 23 is formed from the wall of the inner tube 5, the outer tubing 3 may be coaxially or concentrically disposed around the inner tube 5. The pusher means 23 is configured to translate axially along the length of the catheter, relative to the outer tubing 3.

Where the pusher means 23 is formed of the wall of the inner tube 5, the inner tube 5 may be configured to translate axially along the length catheter, relative to the outer tubing 3. Movement of the pusher means 23 may be effected by operating a plunger 7 mechanically connected to the pusher rod 5 or inner tubing 5, at the proximal end 20 of the catheter 10.

The position of the outer tubing 3 may be maintained or adjusted using a grip area 6. The distal end 21 of pusher means 23 is mechanically attached to the proximal end of the carrier 2.

According to one embodiment of the invention, the catheter 10 comprises, (a) an inner tube 5; (b) an outer tube 3, (c) a pusher means 23. Said outer tube 3 is surrounding at least a portion of the length of said inner tube 5. Said pusher rod 4 may be disposed between said inner tube 5 and said outer tube 3. Alternatively, the pusher means 23 may be formed of the wall of the inner tube 5, in which case the outer tube 3 surrounds at least a portion of the length of said inner tube 5 whose wall forms the pusher means 23. The pusher rod 4 is adapted for axial movement relative to said outer tube. The tubular member 9 is attached to the distal end of the pusher means 23, and may be retracted in the outer tube 3 in the compressed state.

Figure 2A:
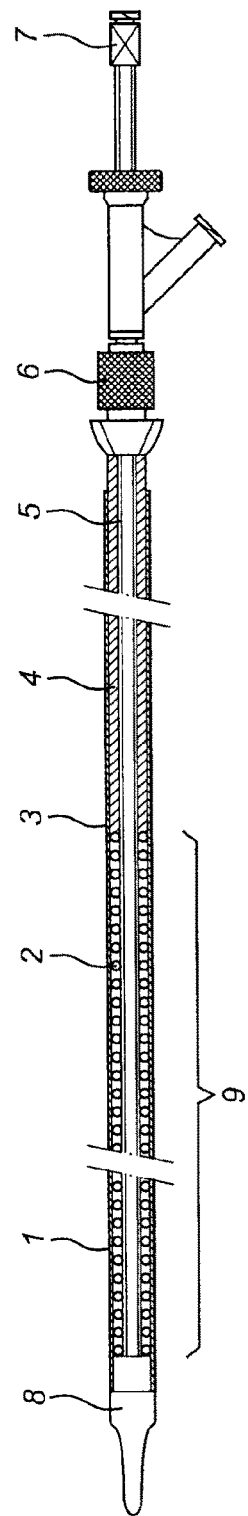
FIG. 2A illustrates an embodiment of the second medical device of FIG. 1 where the tubular member is in its collapsed, compressed state and is provided with a closed tip.
Figure 2B:
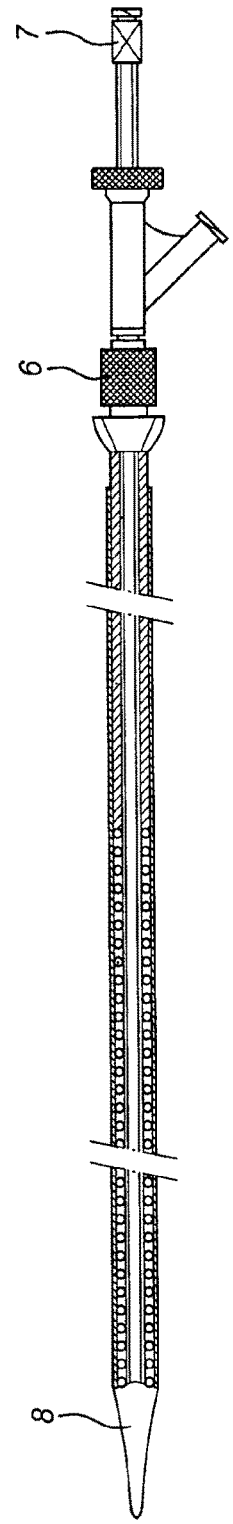
FIG. 2B illustrates another embodiment of the second medical device of FIG. 1 where the tubular member is in its collapsed, compressed state and is provided with a conical closed tip.

FIG. 2 illustrates the tubular member 9, comprising the liner 1 and carrier 2, retracted within the outer tubing 3 of the catheter 10. In the compressed state, the tubular member 9 is maintained compressed by inner surface of the outer tube 3, which acts as a restraint. FIG. 2A shows an embodiment wherein a closed tip 8 is provided to the device at the distal end 21. FIG. 2B shows an embodiment wherein a conical closed tip 8' is provided at the distal end 21 of the device. Said conical closed tip 8' acts as a dilator which helps opening and enlarging the vein during the introduction of the second medical device.

According to one aspect of the invention, the catheter 10 further comprises a restraining member disposed between said outer tube 3 and tubular member 9, said restraining member being dimensioned to maintain said tubular member 9 in a compressed state.

The aforementioned restraining member may be a braided tube—or any other type of tube—surrounding said tubular member 9, said braided tube preferably being made from a strong, flexible, filamentary material having a low coefficient of friction. Examples of such materials may be a fine polyester or metal wire. The braided tube may be formed directly over the tubular member 9, preferably using an automated braiding machine, or may be pre-formed and then inserted over the tubular member 9. Where the braided tube is pre-formed and inserted over the tubular member 9, the system preferably further includes a braid holding sleeve secured to the inner tube 5, said braid holding sleeve being adapted to receive the proximal end of the braided tube. The distal end of the restraining member is preferably mechanically coupled to the distal end of the outer tube 3 so that retraction of the outer tube 3 causes the restraining member to retract from the tubular member 9, thereby allowing the tubular member 9 to self-expand. The catheter 10, and tubular member 9 may be inserted in a blood vessel and, preferably with the aid of a guide wire, maneuvered to its desired position. The guidewire may be disposed with a separate guidewire lumen. Alternatively, the inner tube 5 may act as a guidewire lumen. The tubular member 9 may be deployed by moving the pusher means 23 axially in the distal direction, while the outer tubing 3 is held in a fixed position. Preferably, the tubular member 9 is deployed by retracting the outer tubing 3 axially in the proximal direction while the pusher means 23 is held in a fixed position. The practitioner may position the tubular member appropriately to account for any shortening of the device during deployment. As the restraint of the outer tubing is removed, the tubular member 9 self-expands. The catheter may optionally be closed with a tip 8.

As seen in FIG. 1 the second medical device comprising the liner 1 and carrier 2 expands to its dumb-bell or hour-glass shape. Retrieval of the device after treatment is by withdrawing the tubular member 9 into the outer tubing 3. This may be achieved by drawing the pusher means 23 towards the proximal end 20 while maintaining the position of the outer tubing 3. Alternatively, the outer tubing 3 may be pushed towards the distal end 21 while maintaining the position of the pusher rod 4. Because the carrier 2 is connected to the pusher means 23, the tubular member 9 is forced to take its non-expanded state inside the outer tubing 3 again. The device can then be carefully withdrawn from the blood vessel.

The inner tube 5 of the catheter 10 is in fluid connection with the one or more ports 15 present in the wall tubular member 9. Said port 15 is disposed in the wall of the tubular member 9 in the region of the annular lumen 18. The port 15 may be disposed in the central part 11, and/or in the parts of the annular ridges 12, 13 that form the annular lumen 18. The port 15 allows the lumen of the inner tube 5 to be in fluid contact with the annular lumen 18 so that liquids, e.g. blood, can be withdrawn or collected through the catheter 10 from the annular lumen 18. The port 15 may also act as an entry/exit point for a guidewire.

Whether the second medical device is provided with one or more ports, the size of the ports 15 and the diameter of the inner tube 5 should be selected such as they are not obstructed by the particles if the treatment agent is delivered in said particles. Preferably, the ports are at least 1 mm wide and the diameter of the inner tube is at least 5 mm.

The diameter of the inner tube is preferably >1 mm to prevent the piling up of particles which can occlude the device. The normal blood flow through the liver is about 1.5-1.8 liters/minute. The second retrievable medical device have a French size diameter of F18 (=about 6 mm), preferably the diameter is below F16 (=about 5.3 mm), thereby allowing a flow up to 2 liters/minute.

The skilled person will understand that the connection between the inner tube 5 and the ports 15 can be optimised so that expansion of the tubular member 9 does not result in axial tension in the inner tube 5, or excessive slack along the inner tube 5. According to one embodiment of the invention, the inner tube 5 of the catheter 10 extends from the outer tubing 3 and is in fluid connection with the annular lumen 18 via one or more ports 15. In other words, the inner tube 5 may extend from the outer tubing 3 to connect with the ports 15, as a continuous extension of the inner tube. According to another embodiment of the invention, the inner tube 5 of the catheter 10 is in fluid connection with a port 15 of the tubular member 9 using a bridging tubing.

Figure 5:
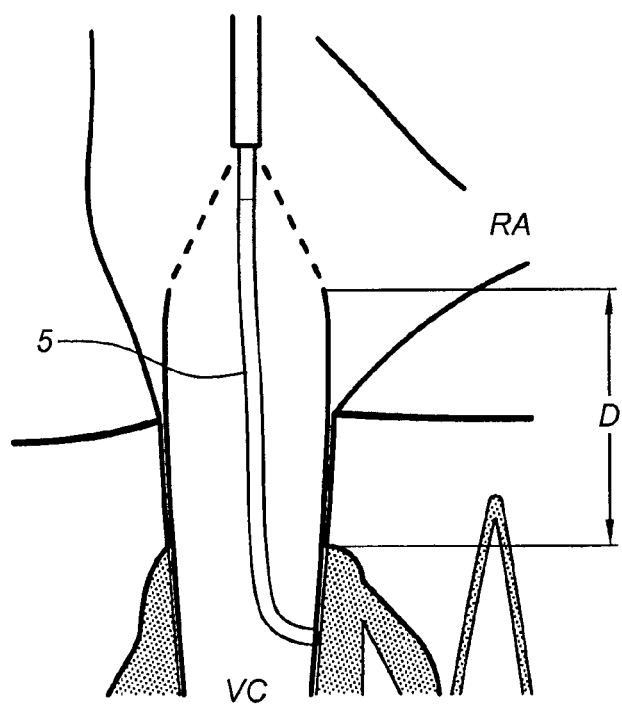
FIG. 5 illustrates the second medical device when introduced in the vena cava.
Figure 6:
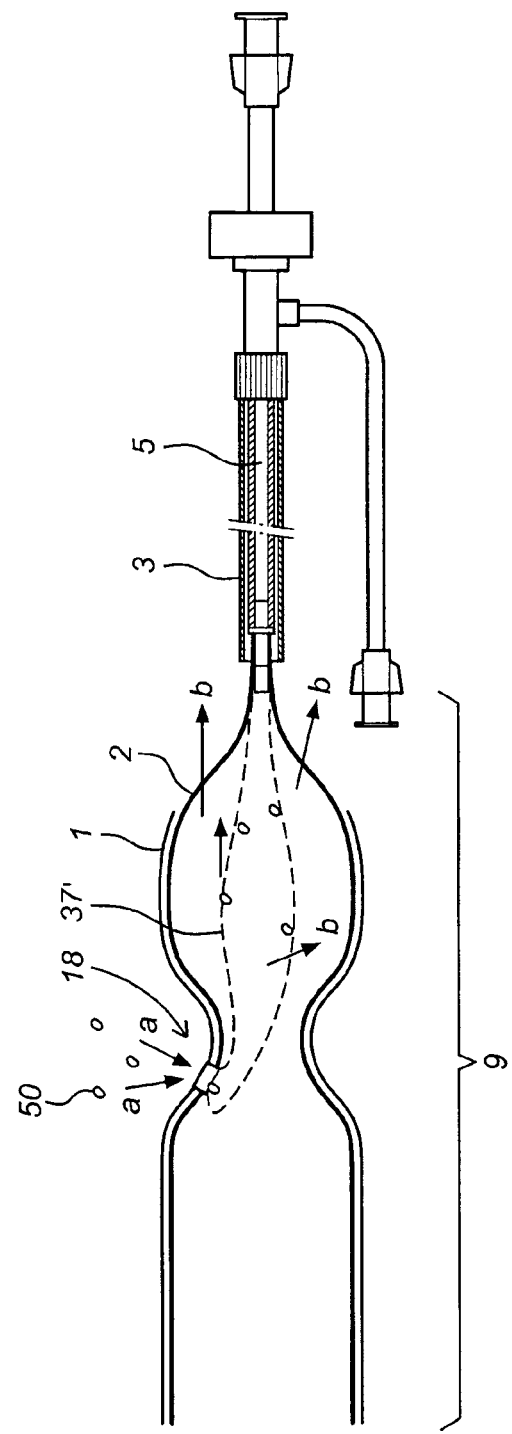
FIG. 6 illustrates an embodiment showing the position of the separation device within the second medical device.
Figure 7:
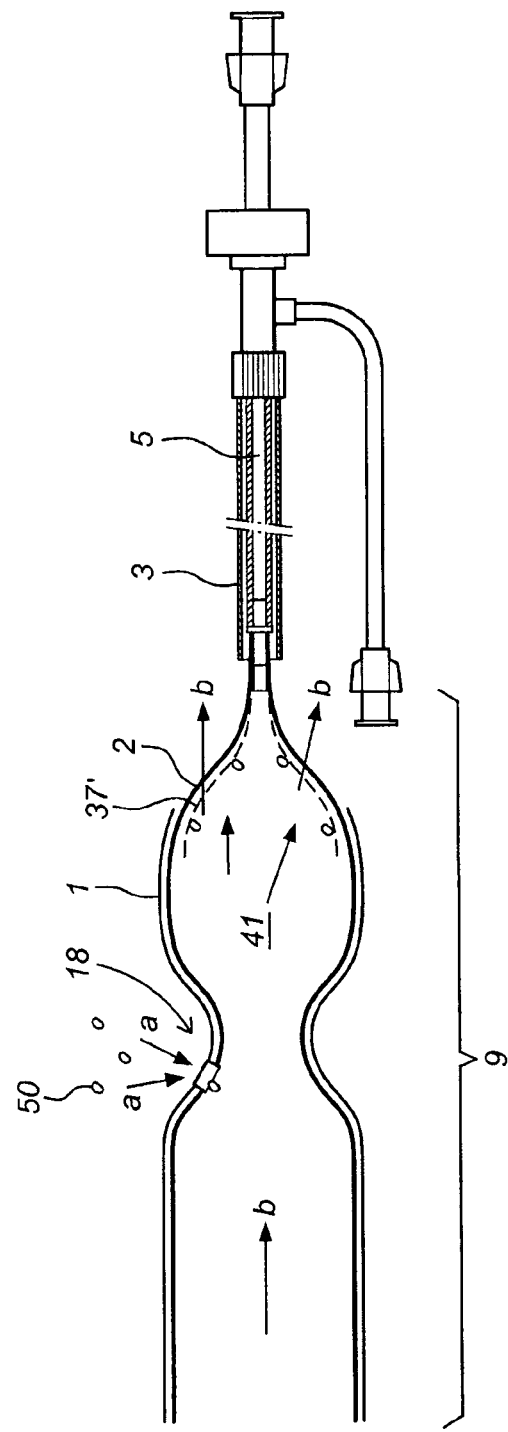
FIG. 7 illustrates another embodiment showing the position of the separation device within the second medical device.

FIG. 5 shows one configuration of the inner tube 5 whereby a rigid bridging tube 19 is employed to connect fluidly a port 15 of the tubular member 9 to the inner tube 5 of the catheter 10. FIG. 6 shows an alternative configuration of the inner tube 5 whereby the separation device is provided with openings 37', and whereby an axially expandable bridging tube 19' is employed to connect fluidly a port 15 of the tubular member 9 to the inner tube 5 of the catheter 10. The latter bridging tubing 19' is typically made from a flexible material which can expand by virtue of elastic properties and/or by use of a concertina-like folding of the unexpanded bridging tube 19'.

Figure 3A:
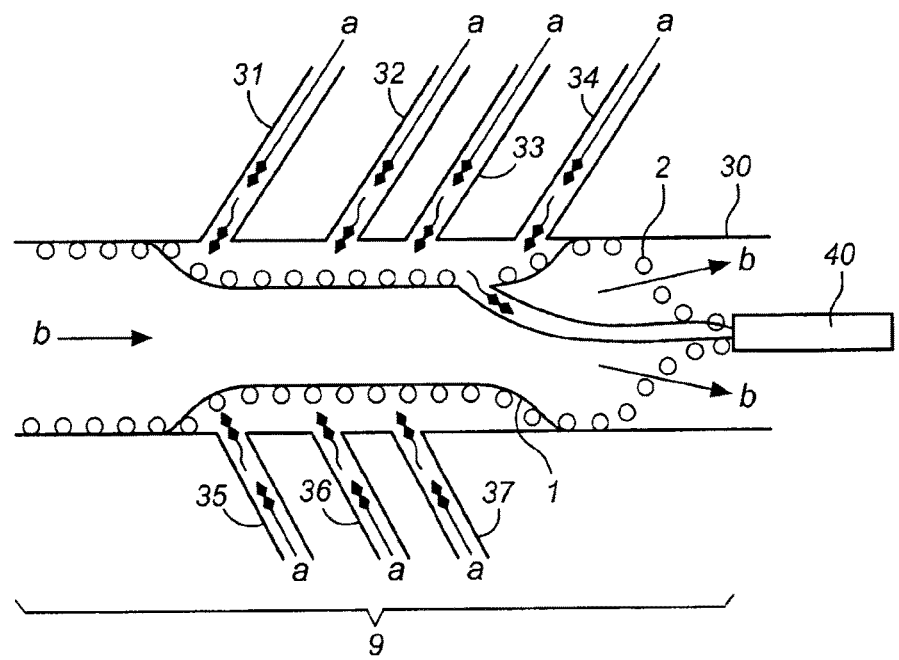
FIG. 3 illustrates the second medical device of the present invention have been placed in situ, wherein: A illustrates a liner on the exterior of the carrier, and B illustrates a liner on the interior of the carrier.
Figure 3B:
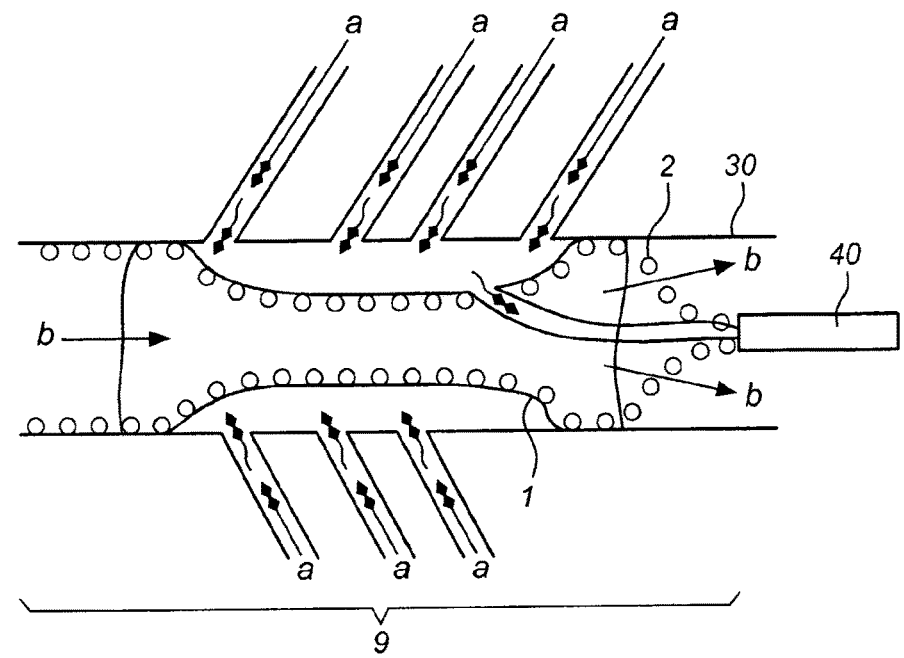
Figure 3C:
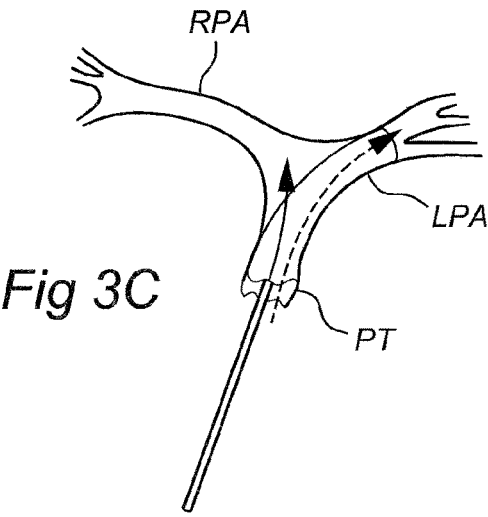
Figure 3D:
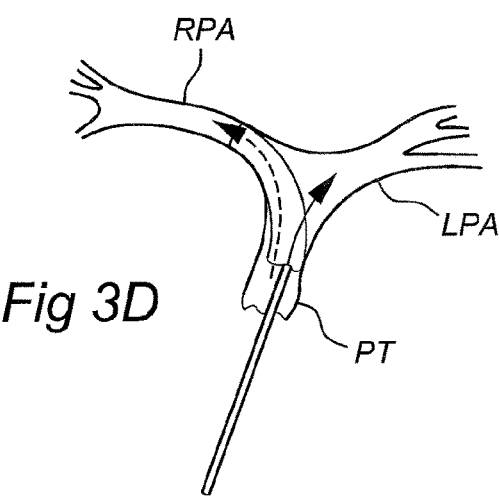
Figure 3E:
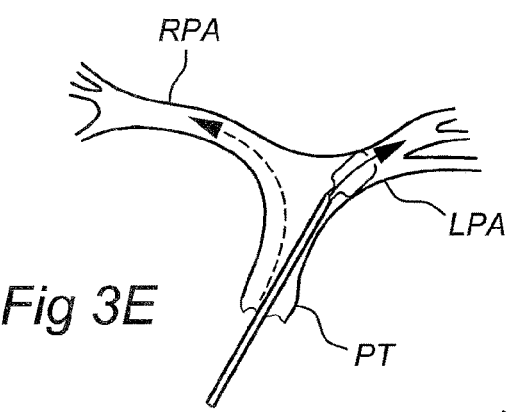
Figure 3F:
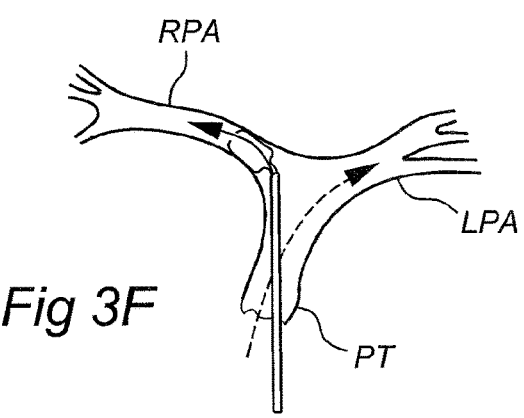

FIGS. 3A and 3B illustrate the system where the tubular member 9 is deployed within a vessel 30. The proximal 13 and distal 12 annular ridges contact the wall of the vessel 30, and the central part 11 forms an annular lumen 18. Blood (illustrated by arrow b) is able to flow freely through the unlined portion of the tubular member 9. The annular lumen 18 may span the region of branched vessels 31 to 37, wherein blood with therapeutic agent excess (illustrated by arrows a) will flow. Blood with therapeutic agent excess (illustrated by arrows a) flows then inside the inner tube 5.

In FIG. 3A, the liner 1 is attached to the carrier 2 such that the liner is on the inside of the carrier 2. FIG. 3B shows an alternative configuration whereby the liner 1 is on the outside of the carrier 2.

The device as described above is particularly useful for the minimal invasive and repeatable treatment of an organ. After positioning, as mentioned, before the device expands to achieve its dumb-bell or hour-glass shape. The proximal annular ridge 13 and distal annular ridge 12 (i.e. the end parts of the device) expand until they press against the inner wall of the vessel, thereby fixing the device at the selected position and providing a liquid tight seal inside the vessel. The central part 11 of the device expands to a lesser degree, thereby creating an annular lumen 18 between the device and the inner wall of the vessel. Inside the device is a passageway lumen 14 for bypassing the systemic blood past the sealed area. This way the passageway lumen 14 defines a new blood path to allow the continuation of the systemic blood flow during perfusion. The liquid tight sealing of the vessel by the proximal annular ridge 13 and distal annular ridge 12 and the liquid tight liner 1 of the device form a liquid tight barrier, separating the systemic blood flowing through the passageway 14 from the blood present in the annular lumen 18. This blood can be collected from the annular lumen 18.

Depending on the type and positioning of the cells for treatment, the practitioner can decide in which vein to introduce the second medical device. During liver treatment, the second medical device id introduced in the vena cava (VC), thereby isolating the blood brought to the VC by the HV.

Although the following describes the use of this system in a retrograde liver perfusion application, the application is only exemplifying. It is clear to a person skilled in the art that this system can also be used for treating other organs than the liver, this orthograde as well as retrograde.

In a preferred embodiment, for organs like liver and lungs wherein retrograde infusion is possible, the second medical device is used for both delivering the therapeutic agent and removing its excess from an organ. The therapeutic agent could be delivered through the outflow of the organ, thereby loading it with a retrograde flow, i.e. against systemic pressure, assuring that it will stay in the organ. After some time the flow can be restored again and this will push the non-bonded therapeutic agent out of the organ and can be conveyed by the VCD catheter.

Third Retrievable Medical Device

The third retrievable medical device is used for the isolation and/or the perfusion of veins. Said third retrievable medical device comprises a distal end, a proximal end, a lumen, an inflation lumen, a balloon at the distal end of the device and a plurality of outlets, said outlets are positioned at the distal end of the balloon or at the proximal end of the balloon. The third medical device will be used to occlude vessels of the organ to be perfused such as to isolate the organ from the systemic blood flow and can be used as connections for perfusion and/or shunting, e.g. Veno-venous bypass.

When liver is treated for example, the main blood vessels connected to the liver are occluded: the vena porta (PV, hepatic portal vein) using the third retrievable medical device, hepatic artery (HA) using the first retrievable medical device and hepatic vein (HV) using the second retrievable medical device to achieve site specific blood isolation and collection. The isolation of the liver vascular system makes it possible to reach high local chemotherapy concentration.

The introduction of the third retrievable medical device and the first medical device can be achieved by means of an introducer sheath. In a preferred embodiment, the third device incorporates a dilator and eliminates the need for a separate introducer sheath. The third retrievable medical device in the PV has a bypass lumen, e.g. for portal veno-venous bypass, an occlusive seal, preferably a balloon, and a lumen for organ perfusion. The PV medical device may be provided with a perfusion port and associated tubing. The seal is placed upstream of the veins into which the PV branches. Due to its position between the liver and the intestinal parts, the PV is difficult to enter. Therefore, the PV can be entered through the liver as practiced for the placement of a Transjugular Intrahepatic Portosystemic Shunt as is commonly understood by one skilled in the art.

The third retrievable medical device in the PV isolates the abdominal blood flow from the perfusion flow in the liver and is the junction for the Veno-Venous-Bypass for draining off blood coming from the abdominal area. The device also represents the connection point for perfusion from or to the portal vein from the organ side.

The third retrievable medical device of the present invention is a single device suitable to isolate and perfuse the PV. Hence, the patient risk is reduced and procedure time is shortened.

Figure 13:
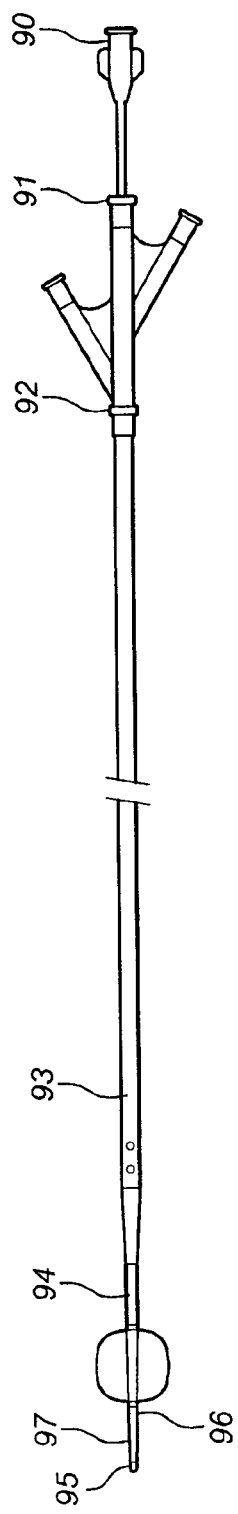
FIG. 13 illustrates an embodiment of the third medical device.

The device is shown in FIG. 13. It is a single device, have small diameter, preferably <F12 (about 4 mm) and easy to place under ultrasonic guidance. The device is provided with at least one balloon that occludes the PV. The device also serves as perfusion and/or infusion catheter for the liver perfusate and can additionally facilitate portal veno-venous bypass.

Figure 9:
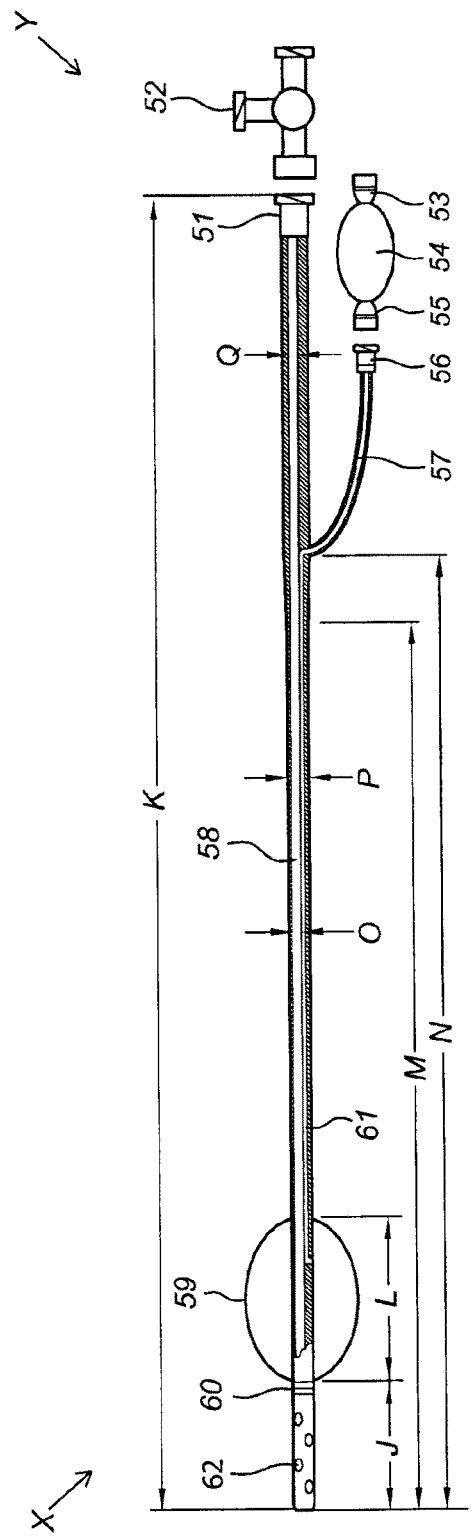
FIG. 9 detailed schematic illustration of an embodiment of the third medical device.
Figure 10:
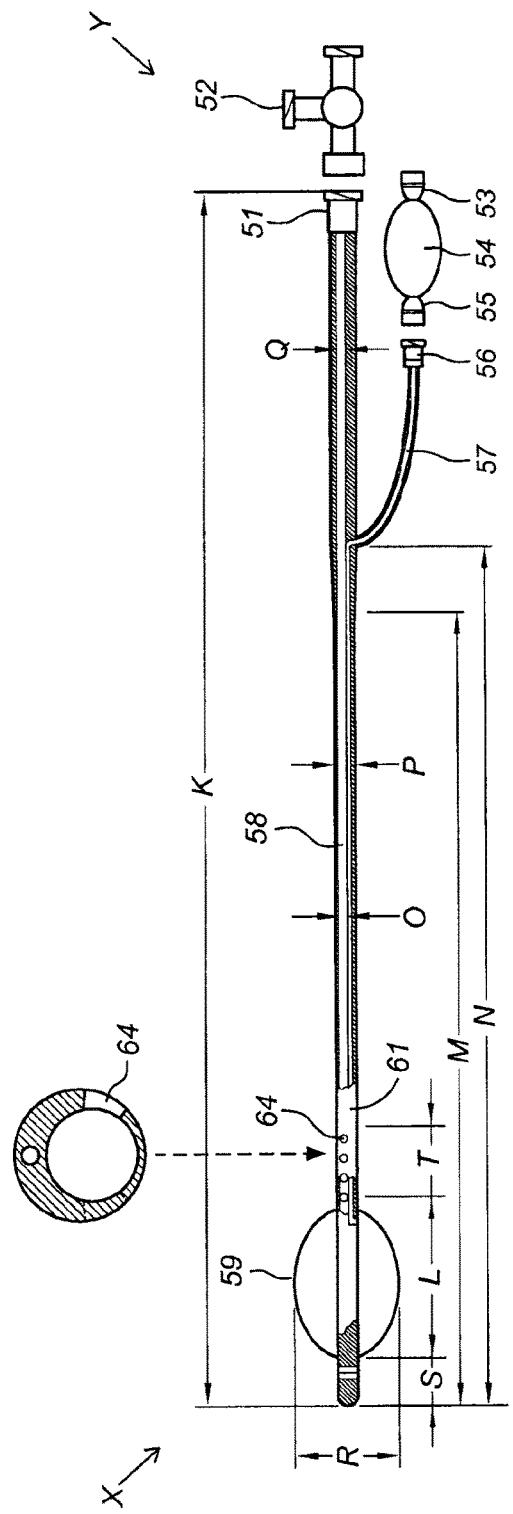
FIG. 10 detailed schematic illustration of another embodiment of the third medical device.

A further detailed illustration of the third retrievable medical device is shown in FIG. 9 and FIG. 10. The third retrievable medical device comprises a tube having a lumen 58 and an inflation lumen 61. The diameter O of said lumen 58 is at least 2 mm while the diameter P of the third retrievable medical device is about 3 mm. The diameter Q of proximal end Y of the third retrievable medical device is about 4 mm. The lumen 58 is provided at the proximal end Y with a female luer adapter 51 and a 4-way hi-flow stopcock 52. The device is provided with a marker band 60 and a balloon 59 that inflates when the user pushes the inflation bladder 54. The latter is provided with an inflation check valve 53 and a male luer adapter 55. The inflation bladder 54 is connected to the inflation lumen 61 via a female luer adapter 56 and a connector tube 57. In the embodiment shown in FIG. 9, the outlets 62 allowing the perfusion and/or drainage are positioned at the distal end X of the balloon 59 of the device and the distance J at the distal end X and over which the outlets 62 are distributed is comprised between 10 and 14 mm. In the embodiment shown in FIG. 10, the outlets 64 allowing the perfusion and/or drainage are positioned at the proximal end Y of the balloon 59. The distance T over which the outlets 62 are distributed is comprised between 15 and 20 mm and the distance S at the distal end X of the balloon is comprised between 4 and 6 mm. The balloon length L is comprised between 10 and 50 mm, preferably between 15 and 40 mm, more preferably between 20 and 30 mm, most preferably around 24 mm. The Veno-Venous-Bypass of the device is preferably up to 800 cc/min while the normal practice setpoint is about 400 cc/min, and the perfusion flow up to 400 cc/min while the normal practice setpoints in the range of 100-200 cc/min. In a preferred embodiment, the third medical device is made of a biocompatible materials generally applied for short term, <60 minutes, endovascular procedures.

Although the present invention has been described with reference to preferred embodiments thereof, many modifications and alternations may be made by a person having ordinary skill in the art without departing from the scope of this invention which is defined by the appended claims.

What is claimed is:

1. A system for the monitoring and the control of a subjects organ perfusion comprising:
   at least one therapeutic agent,
   at least one first retrievable medical device, for the simultaneous or the separate perfusion and occlusion of the vessel of the organ inflow, comprising a body having a distal end, a proximal end, at least one lumen extending between the proximal end and the distal end, at least one opening which is in fluid communication with the lumen for delivering a fluid to said vessel and at least one expandable balloon coupled with the body of the device,
   at least one second retrievable medical device for isolating and collecting the organ outflow, said device is provided with a distal end and a proximal end; wherein said second medical device comprises a catheter suitable for deploying an expanding member; and wherein the proximal end of the expanding member is attached to the distal end of the catheter,
   a fluid storage reservoir having at least one inlet and at least one outlet, wherein said inlet is suitable to be connected to the proximal end of the second retrievable medical device and said outlet is suitable to be connected to the proximal end of the first retrievable medical device,
   at least one pump for withdrawing fluid from the organ and directing said fluid to the fluid storage reservoir through the inlet of said fluid storage reservoir,
   at least one pump for withdrawing fluid from the fluid storage reservoir at a determined flow rate and directing said fluid to the organ inflow,
   at least one marker for real time monitoring of the leak rate from the organ to the systemic blood circulation,
   at least one marker detector positioned upstream of the inlet of the fluid storage reservoir—at least one marker detector positioned in at least one vessel of the systemic blood circulation,
   at least one volume sensor positioned in the fluid storage reservoir,
   at least one pressure detector or measuring the fluid pressure inside the organ to be perfused, and
   at least one interface for receiving and presenting output system data and for controlling and/or adjusting input system data, wherein the output system data comprises the data collected by the pressure detector and the marker detectors; and the input system data comprises the fluid flow rate to be withdrawn from the fluid storage reservoir which is directed to the organ inflow.

2. The system according to claim 1, further comprising a processing unit for adjusting the fluid flow rate which will be withdrawn from the fluid storage reservoir and directed to the organ inflow, wherein said processing unit is implemented with a method for receiving and processing the output system data and sending a signal to the pump comprising the input system data.

3. The system according to claim 1, wherein the output system data received by the processing unit comprises the fluid pressure inside the organ, the fluid flow rate at which fluid is withdrawn from the organ, the amount of marker measured by the detector positioned upstream of the inlet of the fluid storage reservoir and the amount of marker measured by the detector positioned in at least one vessel of the systemic blood circulation.

4. The system according to claim 1, wherein the input system data comprises a determined fluid flow rate at which fluid is withdrawn from the fluid storage reservoir and directed to the organ inflow.

5. The system according to claim 1, wherein the determined fluid withdrawal flow rate from the fluid storage reservoir is determined such as to maintain the fluid pressure inside the organ lower than the pressure of the systemic blood flow.

6. The system according to claim 1, wherein said marker is selected from the group consisting of radiomarkers, dyes such as Indocyanine Green, the therapeutic agent, a therapeutic agent derivative, alkaline phosphatase, gamma glutamyl transpeptidase, ALT, AST, PT, INR, albumin, and bilirubin.

7. The system according to claim 1, wherein the inlet of the fluid storage reservoir is suitable to be connected to the proximal end of the second retrievable medical device using outflow tubings and the outlet of the fluid storage reservoir is suitable to be connected to the proximal end of the first retrievable medical device medical using inflow tubings.

8. The system according to claim 1, further comprising at least one oxygenator positioned downstream of the outlet of the fluid storage reservoir.

9. The system according to claim 1, further comprising at least one heat exchanger positioned downstream of the outlet of the fluid storage reservoir.

10. The system according to claim 1, further comprising at least one filter positioned upstream of the inlet of the fluid storage reservoir.

11. The system according to claim 1, wherein the balloon of the first medical device is provided with an interior which is in fluid communication an inflation lumen through at least one opening positioned in the body of the device.

12. The system according to claim 1, wherein said opening is provided with at least one valve which is movable from a closed position, in which fluid communication of the lumen with the interior of the balloon is prevented, to an open position in which the lumen is in fluid communication with the interior of the balloon.

13. The system according to claim 1, wherein the expanding member of the second retrievable medical device comprises a carrier and an impermeable liner which is bonded to at least a part of the carrier length.

14. The system according to claim 1, further comprising one or more third retrievable medical device for the occlusion of the organ vessels, said device having a proximal end, a distal end, a lumen extending between said proximal and said distal end, a lumen and at least one inflatable balloon for the occlusion of a vessel.

15. The system according to claim 14, wherein the first medical device and/or the second medical device and/or the third medical device are percutaneously introduced into the different organ vessels.

16. The system according to claim 1, wherein the therapeutic agent is a treatment fluid and/or particles comprising a radioactive element.

17. The system according to claim 1, further comprising at least one container containing a physiologic solution which is optionally delivered to the organ for washing said organ before the start of the perfusion and/or when said perfusion is completed.

* * * * *